United States Patent
Suzuki et al.

(10) Patent No.: US 8,460,636 B2
(45) Date of Patent: Jun. 11, 2013

(54) COMPLEX COMPOUND AND MRI PROBE MADE OF SAME

(75) Inventors: Koji Suzuki, Yokohama (JP); Hiroki Hifumi, Kawasaki (JP); Akihiro Tanimoto, Tokyo (JP); Megumi Makino, Kawasaki (JP)

(73) Assignee: Japan Science and Technology Agency, Kawaguchi-Shi (JP)

( * ) Notice: Subject to any disclaimer, the term of this patent is extended or adjusted under 35 U.S.C. 154(b) by 0 days.

(21) Appl. No.: 13/340,204

(22) Filed: Dec. 29, 2011

(65) Prior Publication Data

US 2012/0093735 A1    Apr. 19, 2012

Related U.S. Application Data

(62) Division of application No. 11/885,949, filed as application No. PCT/JP2006/304474 on Mar. 8, 2006, now abandoned.

(30) Foreign Application Priority Data

Mar. 9, 2005  (JP) ................................ 2005-065033

(51) Int. Cl.
    *A61B 5/055*    (2006.01)
(52) U.S. Cl.
    USPC ................... 424/9.3; 424/9.363; 424/9.365
(58) Field of Classification Search
    None
    See application file for complete search history.

(56) References Cited

FOREIGN PATENT DOCUMENTS

| JP | 2001-523650 A | 11/2001 |
|---|---|---|
| WO | WO 99/25389 A2 | 5/1999 |
| WO | WO 9925389 A2 * | 5/1999 |

OTHER PUBLICATIONS

Frullano et al. Chem. Eur. J. 2004, 10, 5205-5217.*
Trokowski et al. Bioconjugate Chem. 2004, 15, 1431-1440.*
Aime, S. et al, "Metal Complexes as Allosteric Effectors of Human Hemoglobin: an NMR Study of the Interaction of the Gadolinium(III) Bis(m-boroxyphenylamide)diethylenetriaminepentaacetic Acid Complex with Human Oxygenated and Deoxygenated Hemoglobin," Biophysical Journal, May 1999, vol. 76, pp. 2735-2743.
Extended European Search Report, dated Mar. 28, 2011, for European Application No. 06715394.0.
Frullano, L. et al, "Towards Targeted MRI: New MRI Contrast Agents for Sialic Acid Detection," Chem. Eur. J., 2004, vol. 10, pp. 5205-5217.
International Preliminary Report on Patentability, Appl. No. PCT/JP2006/304474, Jun. 19, 2007.
JPO International Search Report, Appl. No. PCT/JP2006/304474, Jun. 13, 2006.
USPTO Office Action dated Jun. 30, 2011 for U.S. Appl. No. 11/885,949.

* cited by examiner

*Primary Examiner* — Michael G Hartley
*Assistant Examiner* — Sean R Donohue
(74) *Attorney, Agent, or Firm* — Birch, Stewart, Kolasch & Birch, LLP

(57) ABSTRACT

Novel gadolinium complex compounds responsive to ions and compounds other than zinc ion, as well as MRI probes made of the compounds are disclosed. Since the gadolinium complex compounds of the present invention such as that represented by the following structural formula exhibit responsiveness to potassium ion, calcium ion, glucose or the like, by using the gadolinium complex compounds of the present invention as a MRI probe, the ion or compound in a living body can be detected and concentration distribution thereof may be determined.

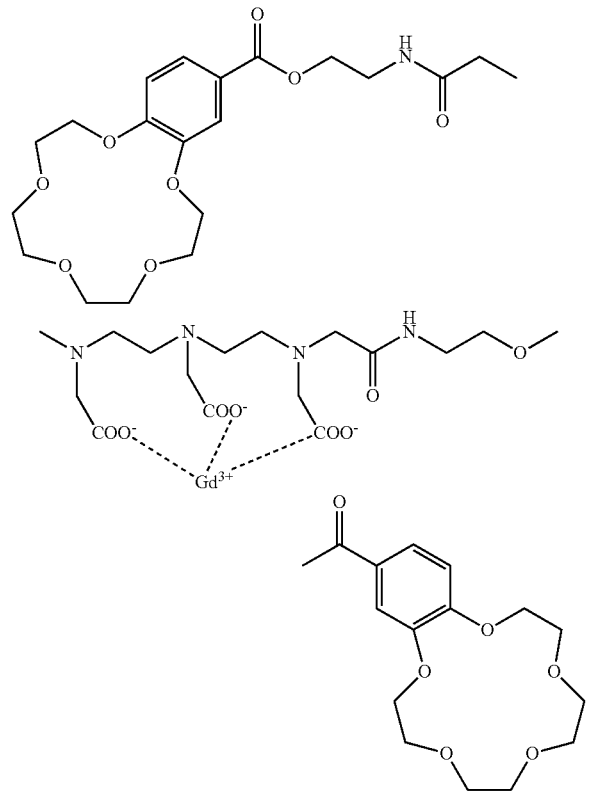

KMR-K001

8 Claims, 6 Drawing Sheets

COMPLEX COMPOUND AND MRI PROBE MADE OF SAME

This application is a Division of co-pending application Ser. No. 11/885,949, filed on Feb. 19, 2008 now abandoned, which is the national stage of PCT International Application No. PCT/JP2006/304474, filed Mar. 8, 2006. This application also claims the benefit of priority of Japanese Patent Application No. 2005-065033, filed Mar. 9, 2005. The entire contents of all are hereby incorporated by reference.

TECHNICAL FIELD

The present invention relates to a gadolinium complex compound and an MRI probe consisting essentially of the same.

BACKGROUND ART

Diagnostic imaging in the medical field is an indispensable medical technology in view of early detection of lesions, preoperative diagnosis, postoperative follow-up diagnosis and so on. Diagnostic imaging methods widely used now in the medical field include CT (computed tomography), MRI (magnetic resonance imaging) and PET (positron emission tomography). However, in CT, exposure to X-ray is unavoidable, and in PET, exposure to γ-ray is unavoidable. In recent years, by virtue of developments in performance of the apparatuses, imaging of multi-sections can be attained. However, increase in exposure dose thereby imposes a further burden to patients. On the other hand, MRI is a noninvasive diagnostic imaging method free from radiation exposure, and has an advantage in that an image of an arbitrary section can be obtained. MRI equipments make images receiving nuclear magnetic resonance signals from the hydrogen atoms contained in water, fat and other components in human body. Therefore, it is theoretically impossible to directly image a physiological action such as metabolism or to image molecules in a living body, which do not have a hydrogen nucleus, and what is actually done by the MRI equipments is nothing more than imaging of density distribution of hydrogen atoms in water. Studies of MRI progressed in the improvements and developments of imaging methods such as pulse sequence, analysis method and of the equipments. However, history of the studies on the contrast agents at a molecular level taking the principle of MRI into consideration is short, and the number of reports thereon is small.

To promote the sensitivity of MRI, MRI contrast agents are widely used. MRI contrast agents clinically and usually used now include gadolinium complex type such as Magnevist (registered trademark) and ProHance (registered trademark), and supermagnetic particle type such as Feridex (registered trademark) consisting of iron oxide $(Fe_2O_3)_m(FeO)_n$. However, the molecules of these contrast agents do not have a function to recognize a specific guest molecule. Even if a contrast agent is administered to the body by intravenous injection or the like, the contrast agent is not distributed to the targeted site in the body. When the supermagnetic particles are administered to the body, they are accumulated specifically in the liver due to the metabolic pathway, and are then subjected to glucuronidation and biliary excretion.

MRI probes in which a specific group is bound to the widely used gadolinium complex have been reported (Patent Literatures 1-3), which are responsive to zinc ion by coordination of the group to zinc ion. However, no gadolinium complex-based MRI probe responsive to an ion or compound other than zinc ion is known.

Non-patent Literature 1: K. Hanaoka et al., Chemistry & Biology 2002, 9, 1027-1032

Non-patent Literature 2: Wen-hong Li et al., J. Am. Chem. Soc. 1999, 121, 1413-1414

Non-patent Literature 3: Wen-hong Li et al., Inorg. Chem. 2002, 41, 4018-4024

DISCLOSURE OF THE INVENTION

Problems to be Solved by the Invention

Accordingly, an object of the present invention is to provide a novel gadolinium complex compound responsive to an ion or compound other than zinc ion, as well as an MRI probe made thereof.

Means for Solving the Problems

The present inventors intensively studied to succeed in creating a novel MRI probe responsive to potassium ion, calcium ion or glucose, by binding a specific group to a specific site of gadolinium complex skeleton used as an MRI probe, thereby completing the present invention.

That is, the present invention provides a gadolinium complex compound represented by the following Formula (1) or (2):

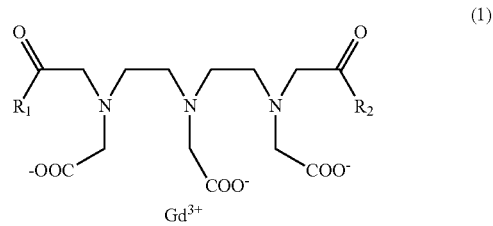

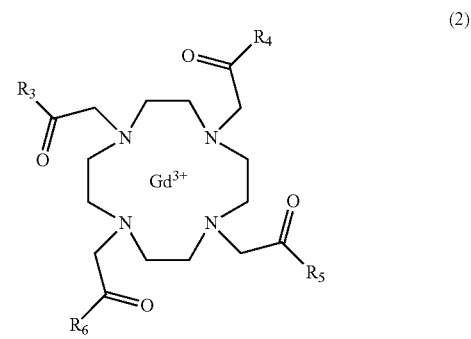

(wherein in Formulae (1) and (2), $R_1$ and $R_2$ are independently a group represented by any of the following Formulae (3), (4), (5), (6) and (7); $R_3$, $R_4$, $R_5$ and $R_6$ are independently —OH or a group represented by any of the following Formulae (3), (4), (5), (6) and (7) with the proviso that two of $R_3$, $R_4$, $R_5$ and $R_6$ are —OH and the other two of them are independently a group represented by any of the following Formulae (3), (4), (5), (6) and (7):

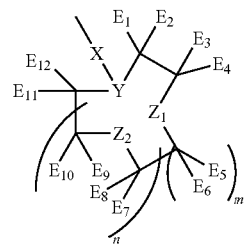

(3)

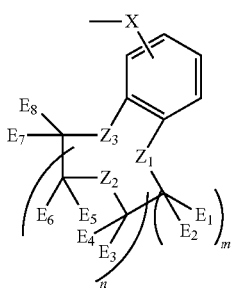

(4)

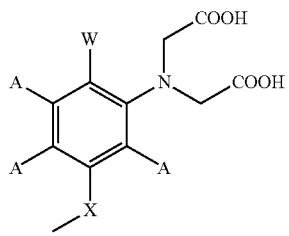

(5)

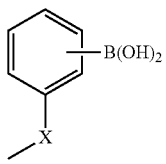

(6)

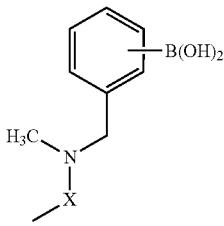

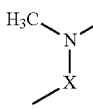

(7)

(wherein in Formulae (3), (4), (5), (6) and (7), X is an alkylene group (wherein one or more carbon atoms constituting the alkylene chain may be an oxygen atom(s), nitrogen atom(s), sulfur atom(s), silicon atom(s), phosphorus atom(s) or carbonyl group(s))

m is 1 or 2; n is an integer of 1 to 8;

Y is a nitrogen atom, sulfur atom or =CH—;

$Z_1$, $Z_2$ and $Z_3$ are independently an oxygen atom, nitrogen atom or sulfur atom;

$E_1$, $E_2$, $E_3$, $E_4$, $E_5$, $E_6$, $E_7$, $E_8$, $E_9$, $E_{10}$, $E_{11}$ and $E_{12}$ are independently a hydrogen atom or an alkyl group (wherein one or more carbon atoms constituting the alkyl chain may be an oxygen atom(s), nitrogen atom(s), sulfur atom(s), silicon atom(s) or phosphorus atom(s)), wherein $E_1$, $E_2$, $E_3$ and $E_4$ may together form a benzene ring, $E_5$, $E_6$, $E_7$ and $E_8$ may together form a benzene ring, and $E_9$, $E_{10}$, $E_{11}$ and $E_{12}$ may together form a benzene ring;

"A"s are independently a hydrogen atom or fluorine atom;

W is —$OCH_3$, a hydrogen atom or fluorine atom).

The present invention also provides an MRI probe consisting essentially of the above-described gadolinium complex compound of the present invention. The present invention also provides a use of the above-described gadolinium complex compound of the present invention for the production of an MRI probe. The present invention further provides a method for measuring potassium ion, calcium ion or glucose in a living body, the method comprising administering the MRI probe of the present invention to the living body.

Effects of the Invention

By the present invention, a novel gadolinium complex compound responsive to an ion or compound other than zinc ion, as well as an MRI probe consisting essentially thereof was first provided. Since the gadolinium compound of the present invention is responsive to potassium ion, calcium ion, glucose or the like, the ion or compound in a living body can be detected and concentration distribution thereof may be determined.

BEST MODE FOR CARRYING OUT THE INVENTION

Figure 1:
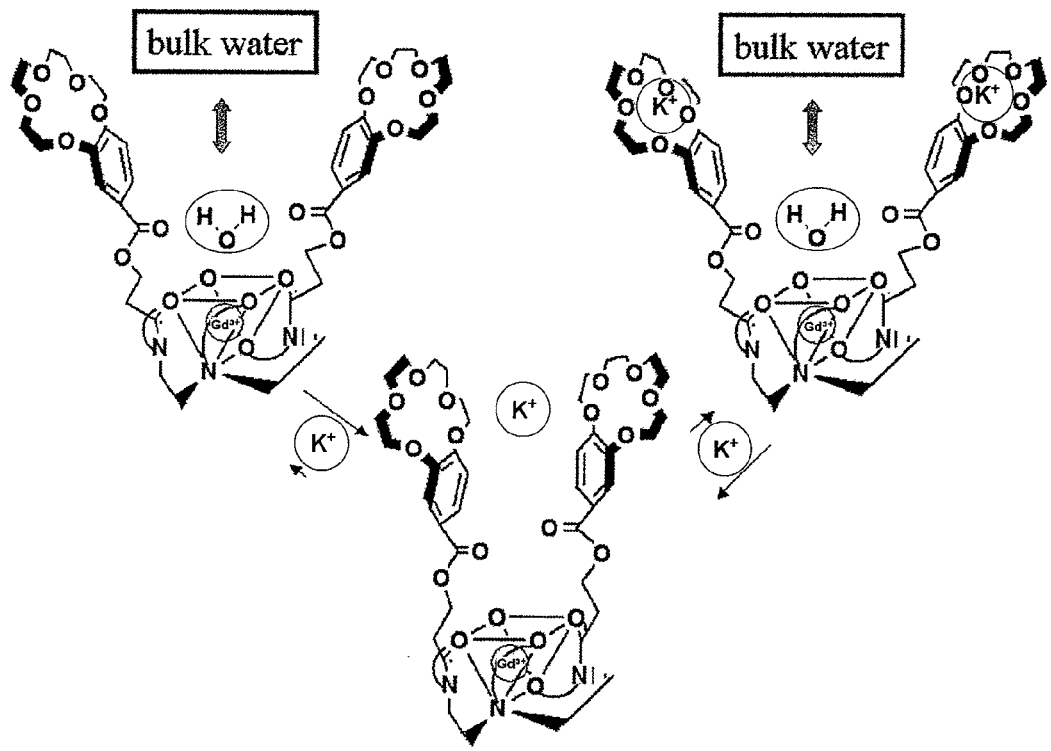
FIG. 1 is a drawing for explaining the manner in which the potassium-responsive MRI probe according to the present invention changes the state of coordination between water molecule and gadolinium ion depending on the concentration of potassium ion.

As described above, the gadolinium complex compound according to the present invention has a structure represented by the above-described Formula (1) or (2). The basic skeleton thereof, that is, the moiety other than $R_1$ and $R_2$ in Formula (1) or the moiety other than $R_3$, $R_4$, $R_5$ and $R_6$ in Formula (2), is the gadolinium complex widely used in MRI probes. The compound of the present invention is the known gadolinium complex to which a specific group is bound to a specific site thereof so as to give responsiveness to a specific ion or compound. Regardless whether the compound has a basic skeleton of the gadolinium complex represented by Formula (1) or (2), the compound exhibits similar performance. However, the compound having the basic skeleton represented by Formula (1) has an advantage that it may be synthesized more easily.

The compounds wherein $R_1$ and $R_2$ in Formula (1), or wherein $R_3$, $R_4$, $R_5$ and $R_6$ in Formula (2) (these groups are hereinafter collectively referred to as "specific responsiveness-imparting group" are represented by Formula (3) or (4) exhibit responsiveness to potassium ion. The compounds wherein the specific responsiveness-imparting groups are represented by Formula (5) exhibit responsiveness to calcium ion. The compounds wherein the specific responsiveness-imparting groups are represented by Formula (6) or (7) exhibit responsiveness to glucose. Each of these will now be described.

In the above-described Formulae (3) and (4), X is an alkylene group (wherein one or more carbon atoms constituting the alkylene chain may be an oxygen atom(s), nitrogen atom(s), sulfur atom(s), silicon atom(s), phosphorus atom(s) or carbonyl group(s)), preferably a $C_1$-$C_{10}$ alkylene group (wherein one or more carbon atoms constituting the alkylene chain may be an oxygen atom(s), nitrogen atom(s), sulfur atom(s), silicon atom(s), phosphorus atom(s) or carbonyl group(s)). m is an integer of 2 or 3, n is an integer of 1 to 8, preferably an integer of 2 to 4. Y is a nitrogen atom, sulfur atom or =CH—. $Z_1$, $Z_2$ and $Z_3$ are independently an oxygen atom, nitrogen atom or sulfur atom, preferably an oxygen atom. $E_1$, $E_2$, $E_3$, $E_4$, $E_5$, $E_6$, $E_7$, $E_8$, $E_9$, $E_{10}$, $E_{11}$ and $E_{12}$ are independently a hydrogen atom or an alkyl group (wherein one or more carbon atoms constituting the alkyl chain may be an oxygen atom(s), nitrogen atom(s), sulfur atom(s), silicon atom(s) or phosphorus atom(s)), and $E_1$, $E_2$, $E_3$ and $E_4$ may together form a benzene ring, $E_5$, $E_6$, $E_7$ and $E_8$ may together form a benzene ring, and $E_9$, $E_{10}$, $E_{11}$ and $E_{12}$ may together form a benzene ring. Preferably, $E_1$, $E_2$, $E_3$, $E_4$, $E_5$, $E_6$, $E_7$, $E_8$, $E_9$, $E_{10}$, $E_{11}$ and $E_{12}$ are independently a hydrogen atom or a $C_1$-$C_{10}$ alkyl group (wherein one or more carbon atoms constituting the alkyl chain may be an oxygen atom(s), nitrogen atom(s), sulfur atom(s), silicon atom(s) or phosphorus atom(s)), more preferably, a hydrogen atom or a $C_1$-$C_4$ alkyl group, and most preferably a hydrogen atom.

Preferably, in Formulae (1) and (2), $R_1$ and $R_2$ are independently a group represented by the Formula (4); two of $R_3$, $R_4$, $R_5$ and $R_6$ are —OH and the other two of them are independently a group represented by the Formula (4); in the Formula (4), $E_1$, $E_2$, $E_3$, $E_4$, $E_5$, $E_6$, $E_7$, $E_8$, $E_9$, $E_{10}$, $E_{11}$ and $E_{12}$ are hydrogen atoms; X is a $C_1$-$C_{10}$ alkylene group (wherein one or more carbon atoms constituting the alkylene chain may be an oxygen atom(s), nitrogen atom(s), sulfur atom(s), silicon atom(s), phosphorus atom(s) or carbonyl group(s)); and wherein $Z_1$, $Z_2$ and $Z_3$ are oxygen atoms.

More preferred groups represented by the Formula (4) are those represented by the following Formula (8) or (9):

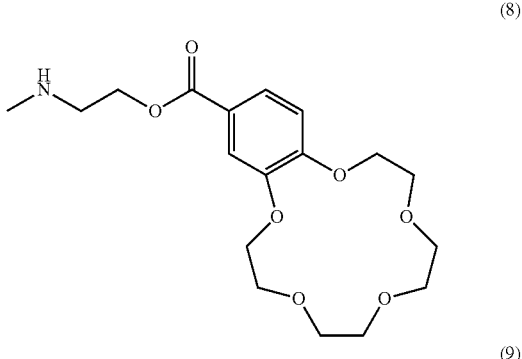

(8)

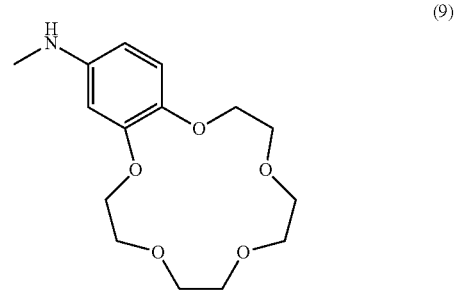

(9)

The gadolinium complex compounds wherein the specific responsiveness-imparting groups are groups represented by the Formula (3) or (4) exhibit responsiveness to potassium ion. The principle thereof will now be explained referring to FIG. 1. FIG. 1 shows the case wherein the specific responsiveness-imparting groups are the group represented by the Formula (8). Gadolinium complexes are most stable when they coordinate with 9 ligands. In the absence of potassium ion, to a gadolinium complex coordinating with 8 ligands, as shown in the left upper drawing in FIG. 1, a water molecule coordinates to the gadolinium complex as the 9th ligand (the coordinated water molecule is sequentially exchanged with the external bulk water after a residence time), so that the longitudinal relaxation time T1 of the hydrogen atom in the water is largely shortened. This is due to the relaxation time-shortening effect by the electron-nuclear dipolar-dipolar interaction, which occurs between the unpaired electron of gadolinium that is a paramagnetic substance and the hydrogen nucleus.

In the presence of potassium ion, the specific responsiveness-imparting groups (in this example, 15-crown-5 ether) trap a potassium ion in a sandwiching manner, so that the water molecule which is the 9th ligand to gadolinium becomes unable to coordinate thereto because of the steric bulkiness (the central lower drawing in FIG. 1). By this, the longitudinal relaxation time-shortening effect by gadolinium is inhibited, so that a large decrease in signals in MRI image (darkening of image) occurs. This occurs when the potassium ion exists not more than about 2 equivalents with respect to the MRI probe. In the presence of a large excess of potassium ion, 15-crown-5 ether and the potassium ion start to form a 1:1 complex (right upper drawing in FIG. 1). By this, the longitudinal relaxation time-shortening effect by gadolinium is gradually exhibited, and as a whole, increase in the signals in MRI image (brightening of image) occurs when compared with the state wherein the amount of potassium ion is about 2 equivalents with respect to the MRI probe.

Thus, in cases where the specific responsiveness-imparting groups represented by Formula (3) or (4) are bound to the gadolinium complex skeleton, contrast of the image differs depending on the presence or absence and concentration of potassium ion. Therefore, by using these gadolinium complex compounds as an MRI probe, images having varying contrasts depending on the potassium ion concentration can be obtained, so that it can be determined where potassium ion exists in the body in what concentration.

The potassium ion in the body is involved in signal transduction, cell growth, cell swelling of nervous cells (rise of potassium ion concentration in intercellular fluid), hyperkalemia (periodic quadriplegia, indications of deterioration of renal function (breathlessness, numbness in limbs, discomfort)), hypokalemia (primary aldosteronism, possibility to stop cardiac muscle), hypertension (Na/K ratio is an index of hypertension) and the like. Thus, determination of the distribution of potassium ion in the body by MRI is useful for diagnosis of these diseases and so on.

The gadolinium complex compounds whose specific responsiveness-imparting groups are represented by the above-described Formula (5) exhibit responsiveness to calcium ion ($Ca^{2+}$). In Formula (5), X is an alkylene group (wherein one or more carbon atoms constituting the alkylene chain may be an oxygen atom(s), nitrogen atom(s), sulfur atom(s), silicon atom(s), phosphorus atom(s) or carbonyl group(s)), preferably a $C_1$-$C_{10}$ alkylene group (wherein one or more carbon atoms constituting the alkylene chain may be an oxygen atom(s), nitrogen atom(s), sulfur atom(s), silicon atom(s), phosphorus atom(s) or carbonyl group(s)). In Formula (5), "A"s are independently a hydrogen atom or fluorine atom, W is —$OCH_3$, a hydrogen atom or fluorine atom.

More preferred group represented by the Formula (5) is the group represented by the following Formula (10):

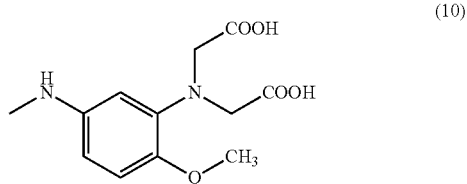 [SMILES: CNc1ccc(OC)c(N(CC(=O)O)CC(=O)O)c1]

(10)

The gadolinium complex compounds of which specific responsiveness-imparting groups are represented by the above-described Formula (5) exhibit responsiveness to calcium ion ($Ca^{2+}$). The principle thereof will now be explained referring to FIG. 2.

As described above, gadolinium complexes are most stable when they coordinate with 9 ligands. As described above about potassium ion, in the absence of calcium ion (left upper drawing in FIG. 2), to a gadolinium complex coordinating with 8 ligands, a water molecule coordinates to the gadolinium complex as the 9th ligand (the coordinated water molecule is sequentially exchanged with the external bulk water after a residence time), so that the longitudinal relaxation time T1 of the hydrogen atom in the water is largely shortened. This is due to the relaxation time-shortening effect by the electron-nuclear dipolar-dipolar interaction, which occurs between the unpaired electron of gadolinium that is a paramagnetic substance and the hydrogen nucleus.

In the presence of calcium ion (central lower drawing in FIG. 2), 4 carboxyl groups (BAPTA structure) trap a calcium ion, so that the water molecule which is the 9th ligand to gadolinium becomes unable to coordinate thereto because of the steric bulkiness. By this, the longitudinal relaxation time-shortening effect by gadolinium is inhibited, so that a large decrease in signals in MRI image (darkening of image) occurs.

Figure 2:
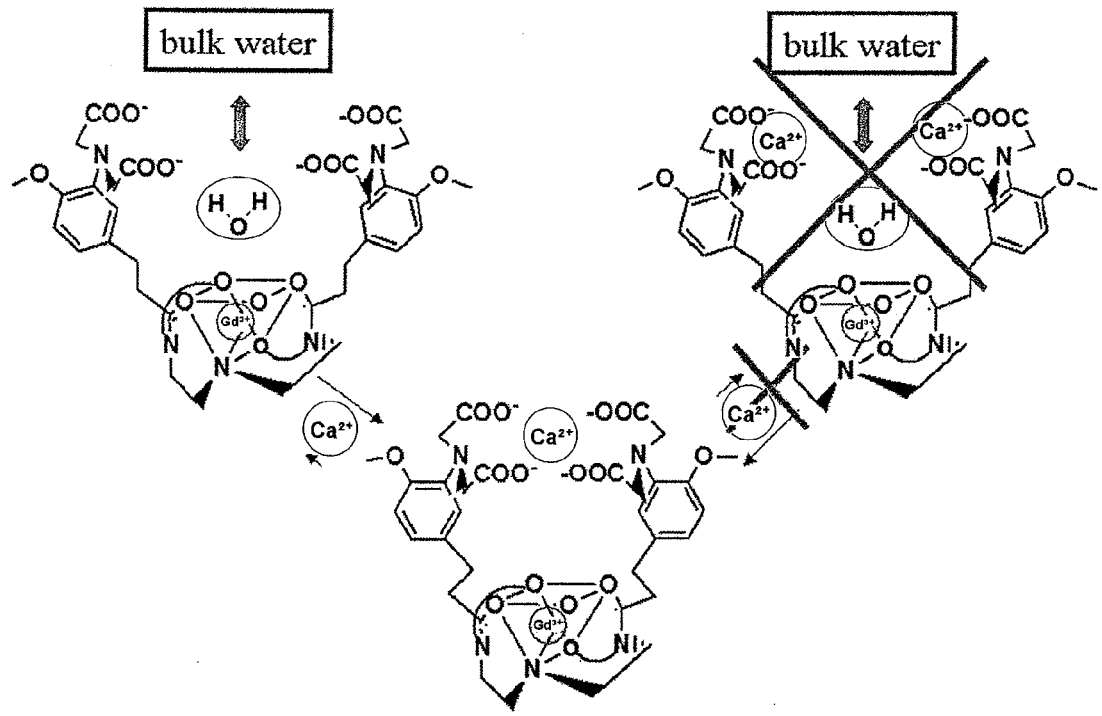
FIG. 2 is a drawing for explaining the manner in which the calcium-responsive MRI probe according to the present invention changes the state of coordination between water molecule and gadolinium ion depending on the concentration of calcium ion.

Unlike the case of MRI probe for potassium ion, since BAPTA forms a very stable complex with calcium ion, the higher the calcium concentration, the more the longitudinal relaxation time-shortening effect is inhibited, so that a large decrease in signals in MRI image (darkening of image) occurs (that is, the state shown in the right upper drawing in FIG. 2 does not occur).

Thus, in cases where the specific responsiveness-imparting groups represented by Formula (5) are bound to the gadolinium complex skeleton, contrast of the image differs depending on the presence or absence and concentration of calcium ion. Therefore, by using these gadolinium complex compounds as an MRI probe, images having varying contrasts depending on the calcium ion concentration can be obtained, so that it can be determined where calcium ion exists in the body in what concentration.

Calcium ion in the body is involved in signal transduction, lesion of hepatic cells (when the cells in the liver are diseased, the function of the cell membrane is first deteriorated and extracellular calcium ion is continuously taken into the cells), gallstone caused by the low calcium level in the blood (renal calculus, gallstone, pancreatic calculus), arteriosclerosis (formation of aneurysm) (these symptoms are caused by the (bad) calcium dissolved from the bones by parathyroid hormone as a result of decrease in blood calcium level) and the like. Thus, determination of the distribution of calcium ion in the body by MRI is useful for diagnosis and the like of these diseases.

The gadolinium complex compounds whose specific responsiveness-imparting groups are represented by the above-described Formula (6) or (7) exhibit responsiveness to glucose. In Formula (6) or (7), X is an alkylene group (wherein one or more carbon atoms constituting the alkylene chain may be an oxygen atom(s), nitrogen atom(s), sulfur atom(s), silicon atom(s), phosphorus atom(s) or carbonyl group(s)), preferably a $C_1$-$C_{10}$ alkylene group (wherein one or more carbon atoms constituting the alkylene chain may be an oxygen atom(s), nitrogen atom(s), sulfur atom(s), silicon atom(s), phosphorus atom(s) or carbonyl group(s)). The groups represented by Formula (7) are more preferred.

Examples of especially preferred groups represented by Formula (7) include those represented by the Formula (11):

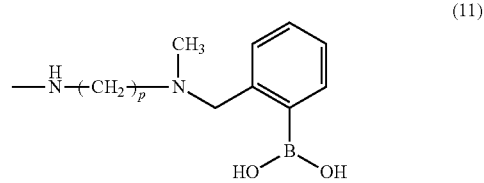

(11)

(wherein in Formula (11), p is an integer of 2 or 3).

Figure 3:
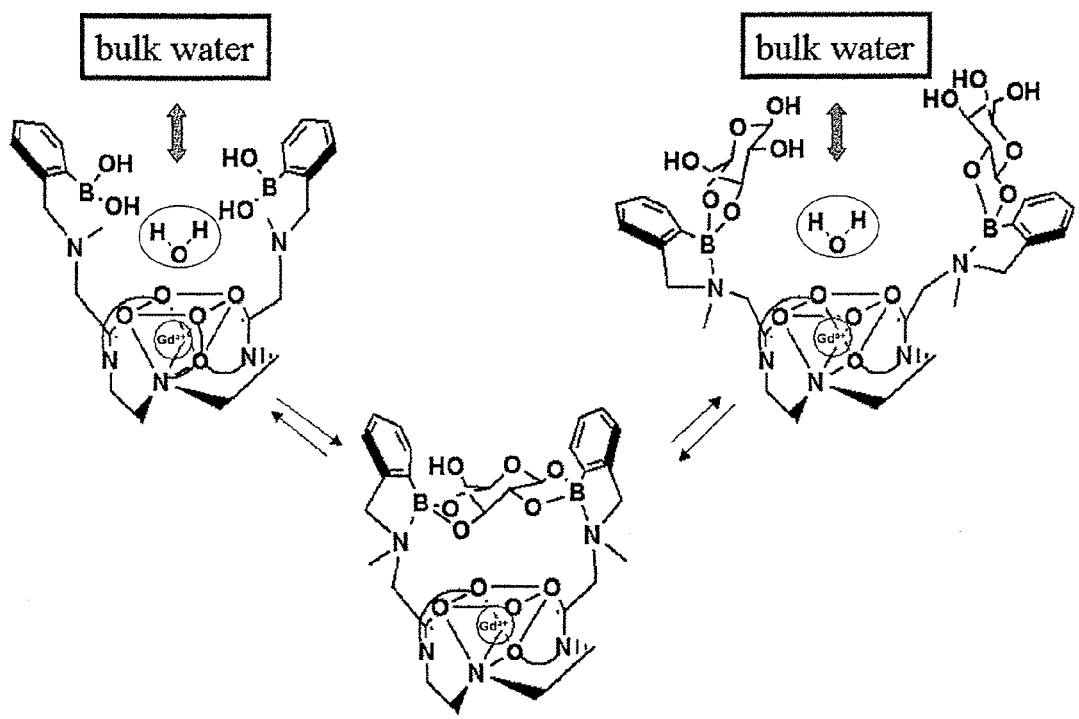
FIG. 3 is a drawing for explaining the manner in which the glucose-responsive MRI probe according to the present invention changes the state of coordination between water molecule and gadolinium ion depending on the concentration of glucose.

The gadolinium complex compounds of which specific responsiveness-imparting groups are represented by the above-described Formula (6) or (7) exhibit responsiveness to glucose. The principle thereof will now be explained referring to FIG. 3.

As described above, gadolinium complexes are most stable when they coordinate with 9 ligands. In the absence of glucose (left upper drawing in FIG. 3), to a gadolinium complex coordinating with 8 ligands, a water molecule coordinates to the gadolinium complex as the 9th ligand (the coordinated water molecule is sequentially exchanged with the external bulk water after a residence time), so that the longitudinal relaxation time T1 of the hydrogen atom in the water is largely shortened. This is due to the relaxation time-shortening effect by the electron-nuclear dipolar-dipolar interaction, which occurs between the unpaired electron of gadolinium that is a paramagnetic substance and the hydrogen nucleus.

In the presence of calcium ion (central lower drawing in FIG. 3), boronic acid moieties trap glucose, so that the water molecule which is the 9th ligand to gadolinium becomes unable to coordinate thereto because of the steric bulkiness. By this, the longitudinal relaxation time-shortening effect by gadolinium is inhibited, so that a large decrease in signals in MRI image (darkening of image) occurs. This occurs when the glucose exists not more than about 1 equivalent with respect to the MRI probe.

In the presence of excess glucose with respect to MRI probe, boronic acid moieties and the glucose start to form a 1:1 complex. By this, the longitudinal relaxation time-shortening effect by gadolinium is gradually exhibited, and as a whole, increase in the signals in MRI image (brightening of image) occurs.

Thus, in cases where the specific responsiveness-imparting groups represented by Formula (6) or (7) are bound to the gadolinium complex skeleton, contrast of the image differs depending on the presence or absence and concentration of calcium ion. Therefore, by using these gadolinium complex compounds as an MRI probe, images having varying contrasts depending on the glucose concentration can be obtained, so that it can be determined where glucose exists in the body in what concentration.

Glucose is the only organic energy source in brain, and blood glucose level is increased in diabetes. Thus, determination of the distribution of glucose in the body by MRI is useful for imaging of energy consumption in the body and energy metabolism in the body, as well as for evaluation of diabetes (such as the evaluation of the capability to secrete insulin, of β cells in pancreas, and the like).

The gadolinium complex compounds according to the present invention can be produced by binding the above-described specific responsiveness-imparting groups to the gadolinium complex skeleton represented by Formula (1) or (2), and finally by applying a gadolinium salt such as gadolinium chloride. The gadolinium complex skeleton represented by Formula (1) or (2) is widely used as MRI probes, and can be produced by a well-known process. The above-described specific responsiveness-imparting groups are also known or can be easily synthesized by those skilled in the art of organic synthetic chemistry from a known compound in accordance with common knowledge of organic synthetic chemistry. Further, since the synthetic processes of the preferred compounds according to the present invention are described in detail in the Examples below, the compounds of the present invention may be easily synthesized referring thereto.

The gadolinium complex compounds according to the present invention can be used as MRI probes. In cases where the compounds are used as an MRI probe, they can be used in the same manner as the usual MRI probes conventionally used. That is, the gadolinium complex compound in an amount effective for the measurement of potassium ion, calcium ion or glucose, and images are taken with an MRI apparatus utilizing the compound as a contrast agent. The term "measure" herein includes both detection and quantification, and also includes examinations of the distribution of the concentration of potassium ion, calcium ion or glucose, as well as the examinations of the change thereof. Usually, an aqueous solution of the probe having a concentration of about 100 mM to 1000 mM is intravenously injected, or injected to the organ or tissue to be observed, in an amount of 0.01 mL/kg to 1 mM/kg, and images are taken with an MRI apparatus utilizing the administered compound as a contrast agent.

The present invention will now be described more concretely by way of examples thereof. However, the present invention is not restricted to the following examples.

Example 1

Synthesis of Potassium Ion-Responsive Gadolinium Complex Compounds KMR-K001 and KMR-K002

According to the following scheme, potassium ion-responsive gadolinium complex compounds KMR-K001 and KMR-K002 were synthesized:

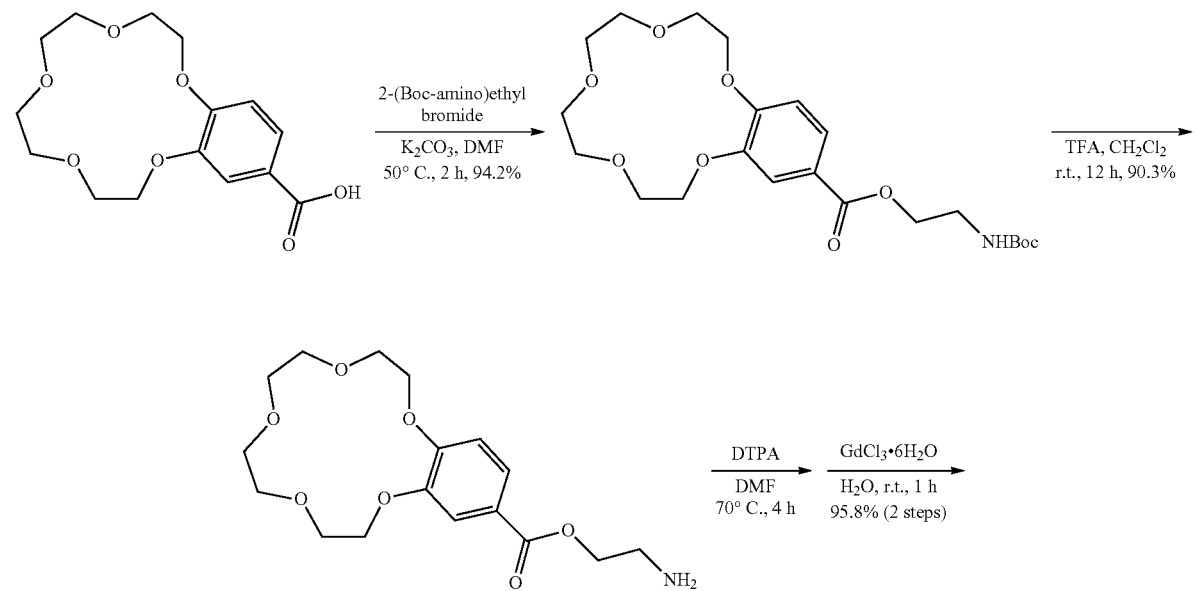

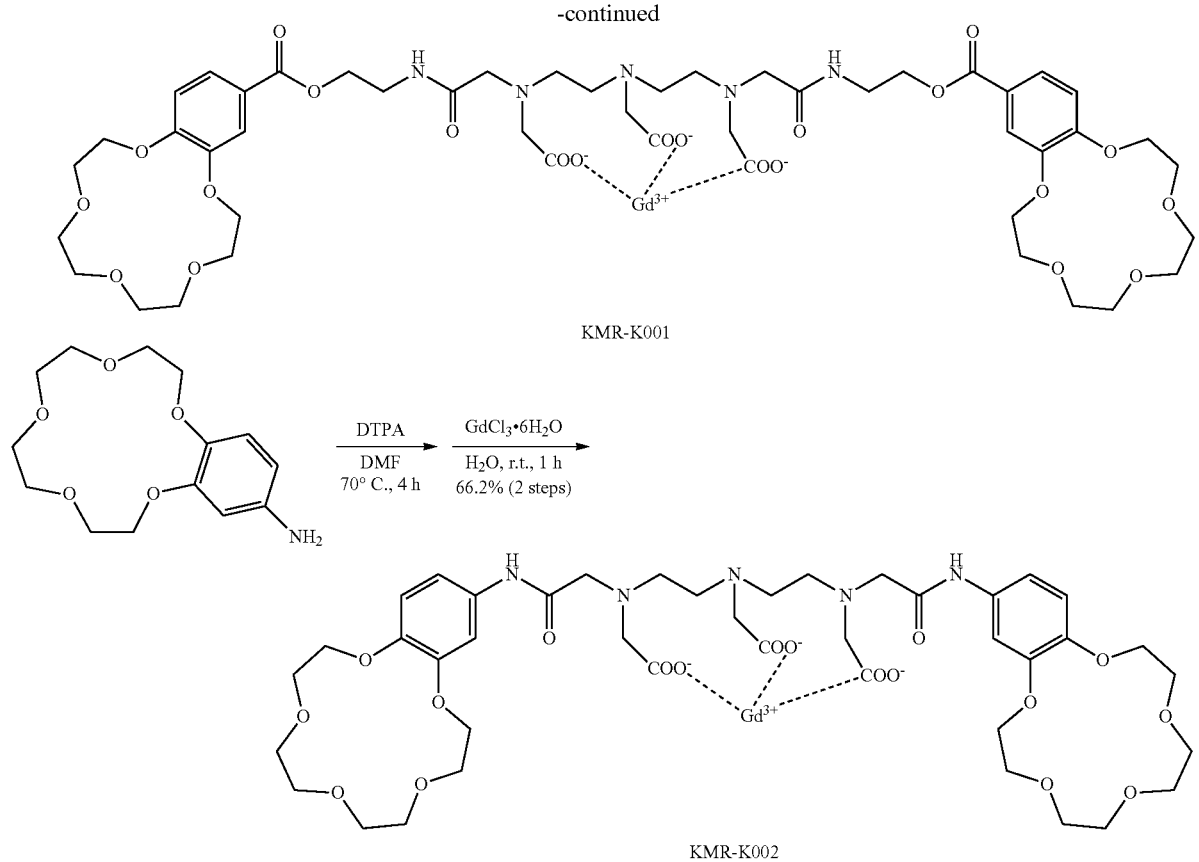

Each step will now be described in detail.

(1) Synthesis of (15-crown-5)-4-benzoic acid 2-tert-butoxycarbonylaminoethyl Ester

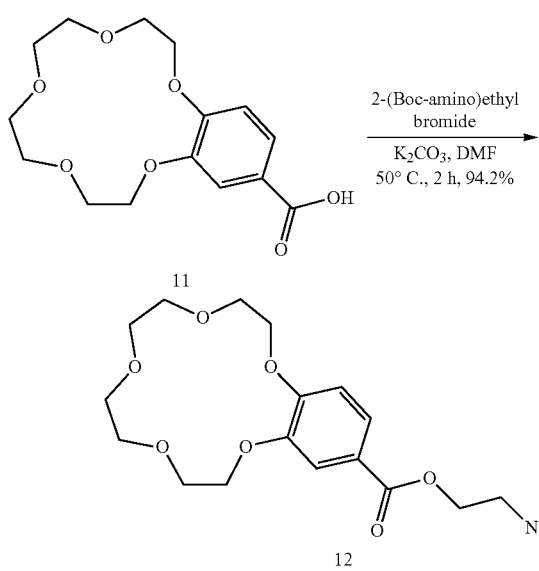

To a solution of mixture of 4-carboxybenzo15-crown-5 (0.77 g, 2.5 mmol, 1.1 equivalent (eq.)) and potassium carbonate (0.93 g, 6.7 mmol, 3.0 eq.) in anhydrous N,N-dimethylformamide (20.0 mL), a solution of 2-(Boc-amino)ethyl bromide (0.50 g, 2.2 mmol, 1.0 eq.) in anhydrous N,N-dimethylformamide (8.0 mL) was added, and the resulting mixture was stirred under Ar atmosphere at 50° C. for 2 hours. The reaction mixture was filtered to remove potassium carbonate. The filtrate was added to dichloromethane (150 mL) and the resulting organic solution was washed with water (100 mL×6). The obtained organic solution was dried over $Na_2SO_4$. The solvent was evaporated under vacuum to obtain yellow crystals (yield: 94.2%).

$^1$H NMR (300 MHz; CDCl$_3$, r.t., TMS, d/ppm) 1.44 (s, 9H, CCH$_3$), 3.50-3.55 (m, 2H, NHCH$_2$), 3.75-3.80 (m, 8H, CH$_2$OCH$_2$CH$_2$OCH$_2$), 3.90-3.95 (m, 4H, ArOCH$_2$CH$_2$O), 4.15-4.20 (m, 4H, ArOCH$_2$CH$_2$O), 4.35 (t, J=5.1 Hz, 2H, CH$_2$OCO), 4.85-4.95 (brs, 1H, NH), 6.85 (d, J=8.3 Hz, 1H, ArH), 7.53 (s, 1H, ArH), 7.67 (d, J=8.3 Hz, 1H, ArH).

TLC: R$_f$=0.4 (SiO$_2$, chloroform:methanol=20:1, v/v)

(2) Synthesis of (15-crown-5)-4-benzoic acid 2-aminoethyl Ester

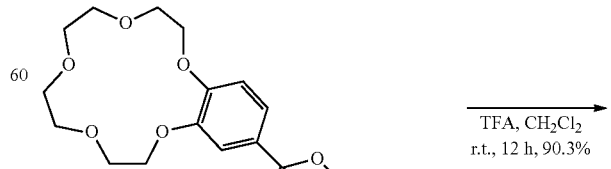

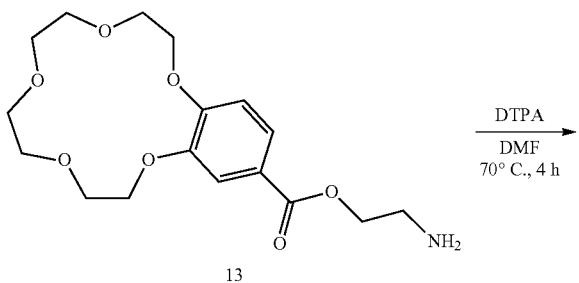

13

To a solution of Compound 12 (50.0 mg, 0.11 mmol, 1.0 eq.) in dichloromethane (1.5 mL), trifluoroacetic acid (0.5 mL) was added and the resulting mixture was stirred at 0° C. for 30 minutes. The solution was then stirred overnight at room temperature. The reaction mixture was evaporated under vacuum, and the residue was purified by column chromatography (SiO$_2$, chloroform:methanol:triethylamine=10:1:0.1, v/v) to obtain an yellow oil (yield: 90.3%).

$^1$H NMR (300 MHz; CDCl$_3$, r.t., TMS, d/ppm) 3.35-3.45 (m, 2H, CH$_2$NH$_2$), 3.60-3.80 (m, 8H, CH$_2$OCH$_2$CH$_2$OCH$_2$), 3.95-4.20 (m, 2H, OCH$_2$), 4.35-4.60 (m, 8H, ArOCH$_2$CH$_2$O), 6.70 (d, J=8.5 Hz, 1H, ArH), 7.40-7.50 (m, 1H, ArH), 7.51 (s, 1H, ArH).

ESI-TOFMS (+), m/z: 356.872 [M+H]$^+$ (calcd. for C$_{17}$H$_{26}$NO$_7^+$: 356.171), 378.904 [M+Na]$^+$ (C$_{17}$H$_{25}$NNaO$_7^+$: 378.152).

TLC: R$_f$=0.2 (SiO$_2$, chloroform:methanol:triethylamine=10:1:0.1, v/v)

(3) Synthesis of [bis-(2-{[(2-carboxy-(benzo-15-crown-5)-ethylcarbamoyl)-methyl]-carboxymethylamino}-ethyl)-amino]-acetic Acid

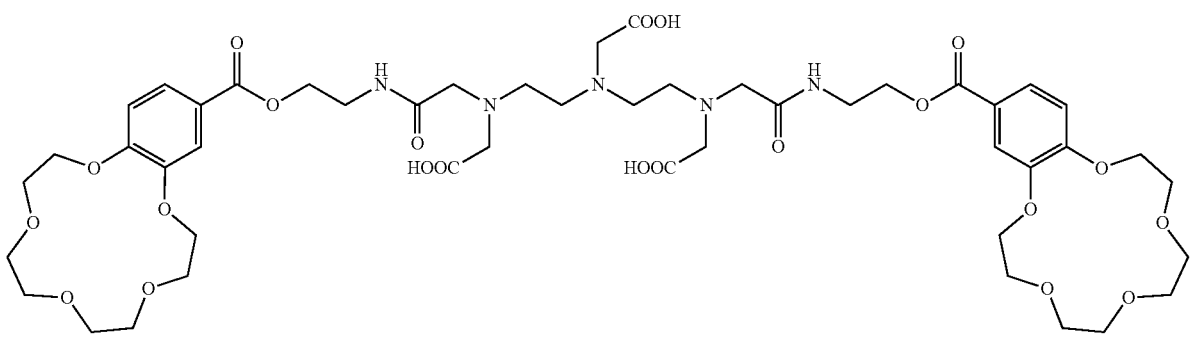

To a mixture of diethylenetriamine pentaacetic acid dianhydride (59.7 mg, 0.17 mmol, 1.0 eq.) and anhydrous N,N-dimethylformamide (0.25 mL), Compound 13 (30.0 mg, 84.0 μmol, 2.0 eq.) was added, and the resulting mixture was stirred under Ar atmosphere at 70° C. for 3 hours. The reaction mixture was evaporated under vacuum to obtain white crude solids.

$^1$H NMR (300 MHz; CD$_3$OD, r.t., TMS, d/ppm) 3.35-3.40 (m, 2H, center NCH$_2$COOH), 3.45-3.55 (m, 8H, NCH$_2$CH$_2$N), 3.55-3.63 (m, 8H, NCH$_2$CONHCH$_2$), 3.64 (s, 4H, NCH$_2$COOH), 3.70-3.75 (m, 16H, CH$_2$OCH$_2$CH$_2$OCH$_2$), 3.85-3.90 (m, 8H, ArOCH$_2$CH$_2$O), 4.10-4.20 (m, 8H, ArOCH$_2$CH$_2$O), 4.35-4.40 (m, 4H, NHCH$_2$CH$_2$), 6.95-7.05 (m, 2H, ArH), 7.50-7.60 (m, 2H, ArH), 7.65-7.70 (m, 2H, ArH).

ESI-TOFMS (+), m/z: 546.024 [M+Na+H]$^{2+}$ (calcd. for C$_{48}$H$_{70}$N$_5$NaO$_{22}^{2+}$: 545.720), 554.012 [M+K+H]$^{2+}$ (calcd. for C$_{48}$H$_{70}$KN$_5$O$_{22}^{2+}$: 553.707), 1069.041 [M+H]$^+$ (calcd. for C$_{48}$H$_{70}$N$_5$O$_{22}^+$: 1068.451).

(4) Synthesis of [bis-(2-{[(2-carboxy-(benzo-15-crown-5)-ethylcarbamoyl)-methyl]-carboxymethyl-amino}-ethyl)-amino]-acetic Acid Gadolinium Complex (KMR-K001)

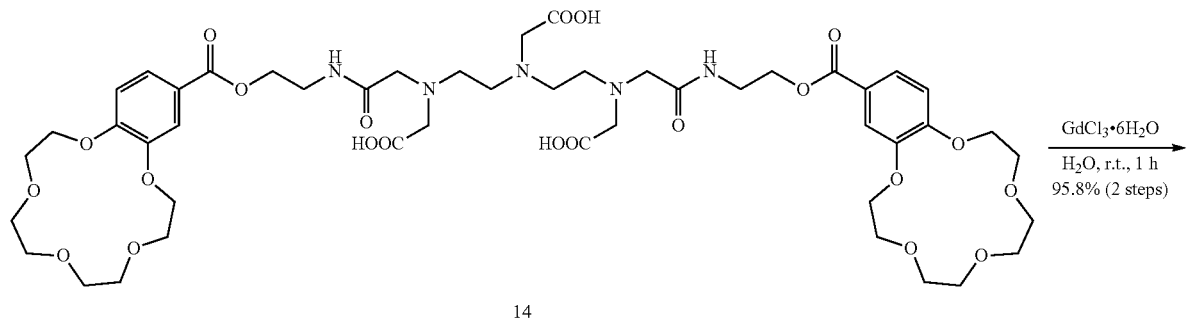

14

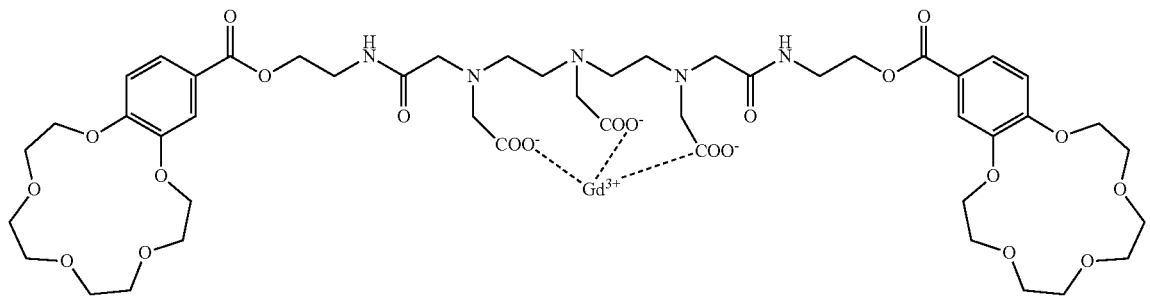

KMR-K001

To a solution of Compound 14 (10.0 mg, 9.4 μmol, 1.0 eq.) in water (4.0 mL), gadolinium(III) chloride hexahydrate (3.1 mg, 8.4 μmol, 0.9 eq.) was added, and the resulting mixture was stirred overnight at room temperature. During this reaction, aqueous NaOH solution was added to keep the pH of the solution at 6. The reaction mixture was then evaporated under vacuum, and the residue was purified by HPLC reverse phase column (methanol:water=3:2, v/v, flow rate: 35 mL/min, retention time: 59 minutes) to obtain white solids (yield: 95.8%).

ESI-TOFMS (+), m/z: 634.937 $[M+2Na]^{2+}$ (calcd. for $C_{48}H_{66}GdN_5Na_2O_{22}^{2+}$: 634.161), 642.940 $[M+K+Na]^{2+}$ (calcd. for $C_{48}H_{66}GdKN_5NaO_{22}^{2+}$: 642.148).

(5) Synthesis of [(2-{carboxymethyl-[2-(carboxymethyl-(benzo-15-crown-5)-carbamoylmethyl-amino)-ethyl]-amino}-ethyl)-phenylcarbamoylmethyl-amino]-acetic Acid

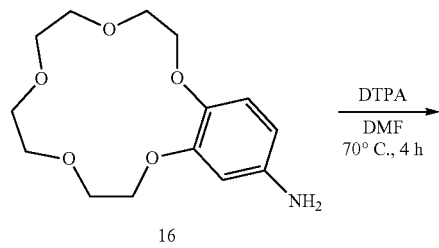

16

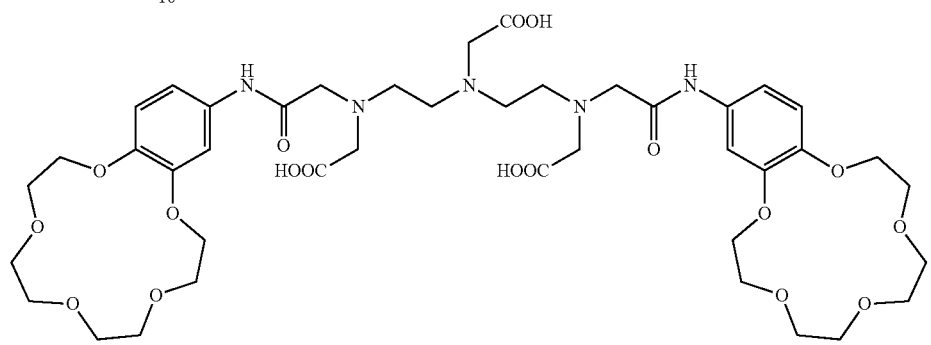

17

To a mixture of diethylenetriamine pentaacetic acid dianhydride (0.32 g, 0.88 mmol, 1.0 eq.) and anhydrous N,N-dimethylformamide (4.0 mL), 4'-aminobenzo-15-crown-5 (0.50 mg, 1.8 mmol, 2.0 eq.) was added, and the resulting mixture was stirred under Ar atmosphere at 70° C. for 4 hours. The reaction mixture was evaporated under vacuum to obtain gray crude solids.

$^1$H NMR (300 MHz; CD$_3$OD, r.t., TMS, d/ppm) 3.20-3.30 (m, 4H, NCH$_2$CH$_2$N), 3.45-3.50 (m, 4H, NCH$_2$CH$_2$N), 3.56 (s, 4H, NCH$_2$COOH), 3.58 (s, 4H, NCH$_2$CONH), 3.65-3.75 (m, 16H, CH$_2$OCH$_2$CH$_2$OCH$_2$), 3.80-3.90 (m, 8H, ArOCH$_2$CH$_2$O), 3.91 (s, 2H, center NCH$_2$COOH), 4.05-4.10 (m, 8H, ArOCH$_2$CH$_2$O), 6.77 (d, J=8.7 Hz, 2H, ArH), 7.07 (d, J=8.4 Hz, 2H, ArH), 7.28 (s, 2H, ArH).

(6) Synthesis of [(2-{carboxymethyl-[2-(carboxymethyl-(benzo-15-crown-5)-carbamoylmethyl-amino)-ethyl]-amino}-ethyl)-phenylcarbamoylmethyl-amino]-acetic Acid Gadolinum Complex (KMR-K002)

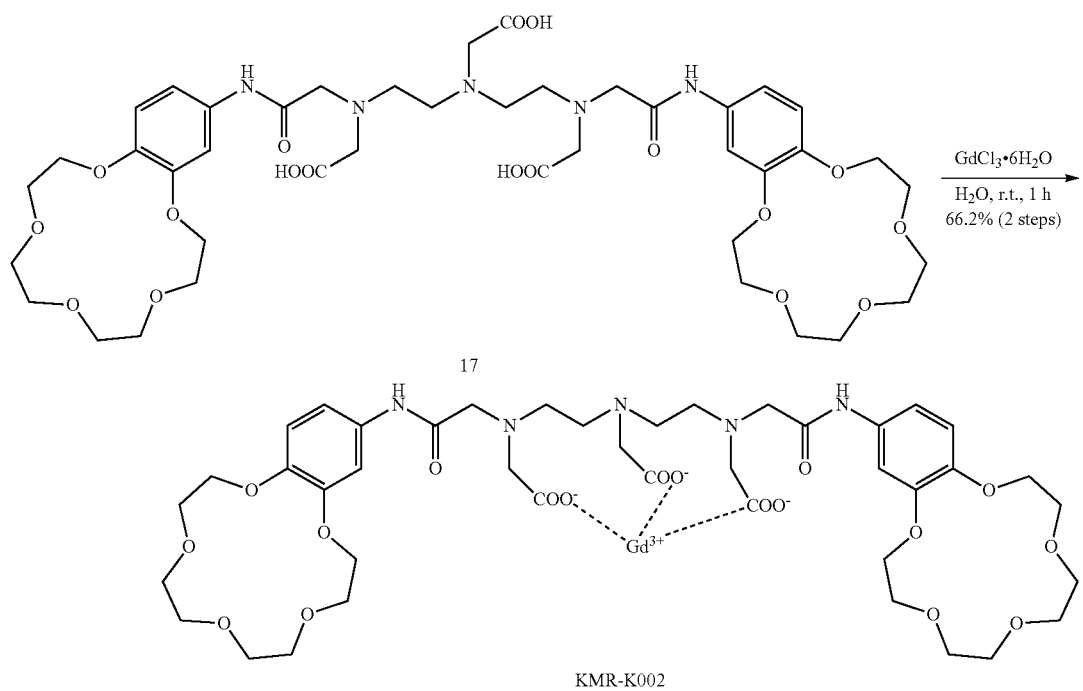

To a solution of Compound 17 (0.10 g, 0.11 mmol, 1.0 eq.) in water (40.0 mL), GdCl$_3$ hexahydrate (36.2 mg, 97.4 μmol, 0.9 eq.) was added, and the mixture was stirred at room temperature for 3 hours. During this reaction, aqueous NaOH solution was added to keep the pH of the solution at 6. The reaction mixture was then evaporated under vacuum, and the residue was purified by HPLC reverse phase column (methanol:water=3:2, v/v, flow rate: 2.5 mL/min, retention time: 67 minutes) to obtain white solids (yield: 66.2%).

ESI-TOFMS (+), m/z: 562.461 [M+2Na]$^{2+}$ (calcd. for C$_{42}$H$_{58}$GdN$_5$Na$_2$O$_{18}$$^{2+}$: 562.140), 551.470 [M+Na+H]$^{2+}$ (calcd. for C$_{42}$H$_{59}$GdN$_5$NaO$_{18}$$^{2+}$: 551.149), 1101.926 [M+H]$^+$ (calcd. for C$_{42}$H$_{58}$GdN$_5$NaO$_{18}$$^+$: 1101.291).

Example 2

Performance of KMR-K001 and KMR-K002

KMR-K001 and KMR-K002 synthesized in Example 1 were examined for the relationship between the potassium ion concentration and longitudinal relaxation time by a conventional method. The measurement conditions were as follows:

[KMR-K001], [KMR-K002]: 0.6 mM measured in 0.05 M Tris/HCl buffer at pH 8.0

KCl was used as K$^+$.

measuring apparatus: NMS 120 minispec NMR ANALYZER produced by

BRUKER (static magnetic field by permanent magnet was 40 MHz, apparatus for measuring longitudinal and transverse relaxation times) was used.

measuring temperature: 40° C.

Figure 4:
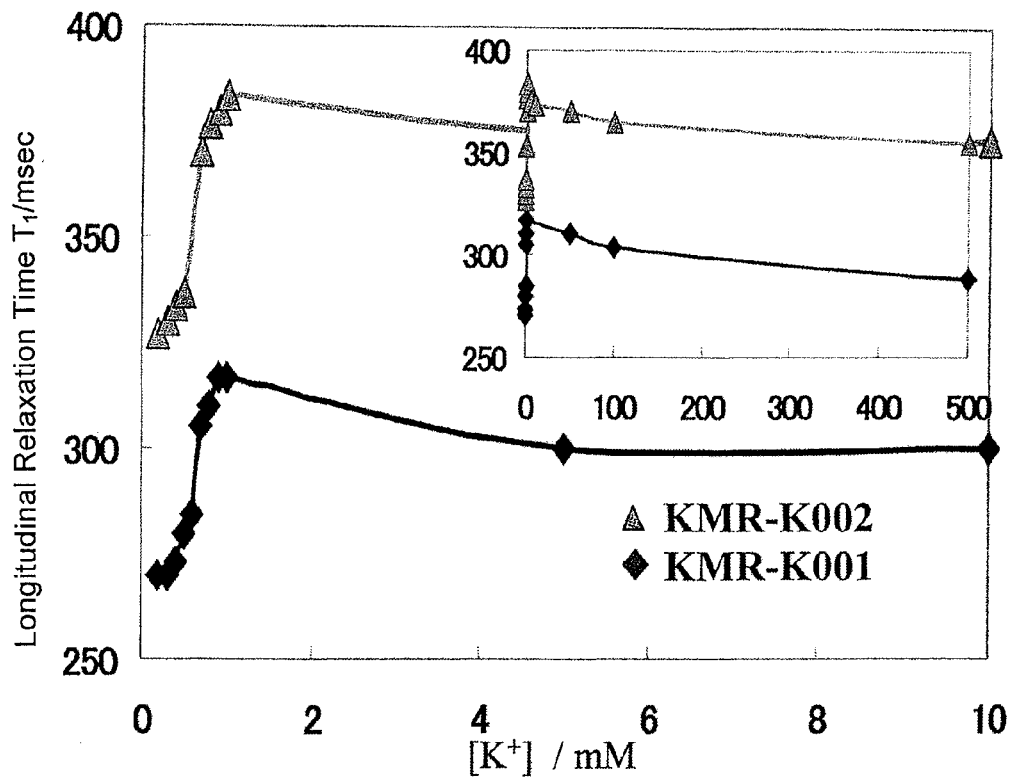
FIG. 4 shows the relationship between the concentration of potassium ion and longitudinal relaxation time of the potassium-responsive MRI probe according to the present invention prepared in an Example.

The results are shown in FIG. 4. As shown in FIG. 4, when the potassium ion was not more than about 2 equivalents with respect to the MRI probe, 15-crown-5 ether and potassium ion formed a sandwich type complex, so that access of water molecules to the gadolinium ion was inhibited and the longitudinal relaxation time monotonically increased. In the presence of a large excess of potassium ion, it is thought that the 15-crown-5 ether and potassium ion formed a sandwich type complex, and the 15-crown-5 ether and potassium ion further formed a complex in which the ratio of the 15-crown-5 ether to potassium ion formed was 1:1. When this 1:1 complex is formed, water molecules can access to the gadolinium ion, so that the longitudinal relaxation time is decreased accordingly. The fact that the more the existing K$^+$, the shorter the longitudinal relaxation time can also be seen from the figure. Comparing KMR-K001 and KMR-K002, although the spacer between the gadolinium complex and the 15-crown-5 ether is longer in KMR-K001 than in KMR-K002, the difference in the responsiveness to K$^+$ due to the difference in the length of the spacer was not observed. With both KMR-K001 and KMR-K002, the longitudinal relaxation time increased maximally by 16 to 17%.

Example 3

Synthesis of Calcium Ion-Responsive Gadolinium Complex Compounds KMR-Ca001

According to the following scheme, a calcium ion-responsive gadolinium complex compound KMR-Ca001 was synthesized:

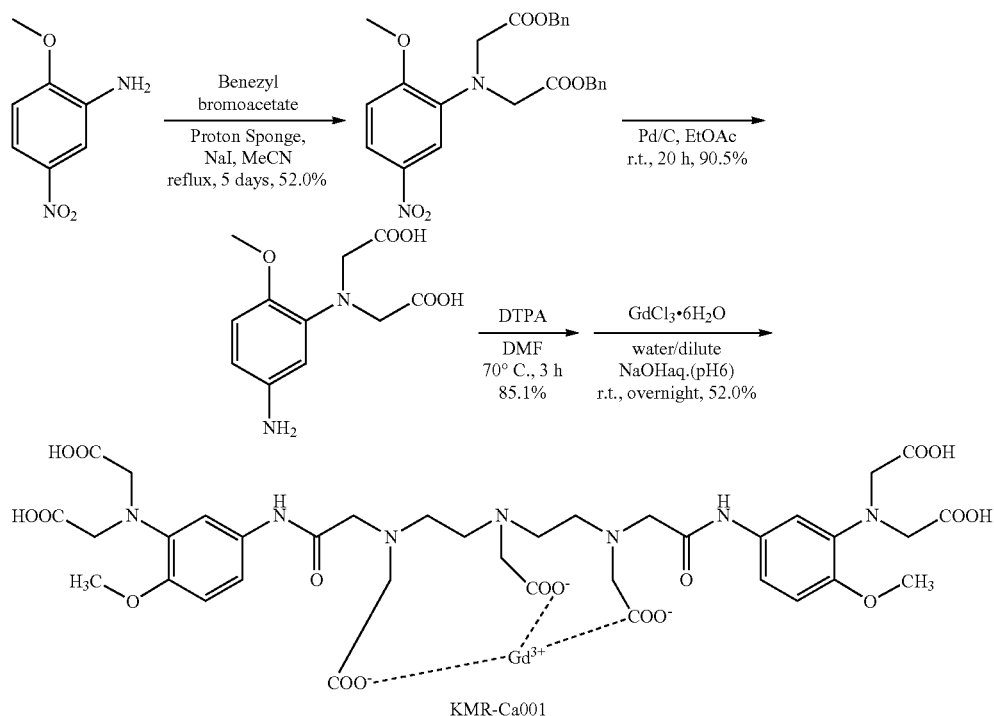

KMR-Ca001

Each step will now be described in detail.

(1) Synthesis of [benzyloxycarbonylmethyl-(2-methoxy-5-nitro-phenyl)-amino]-acetic Acid Benzyl Ester

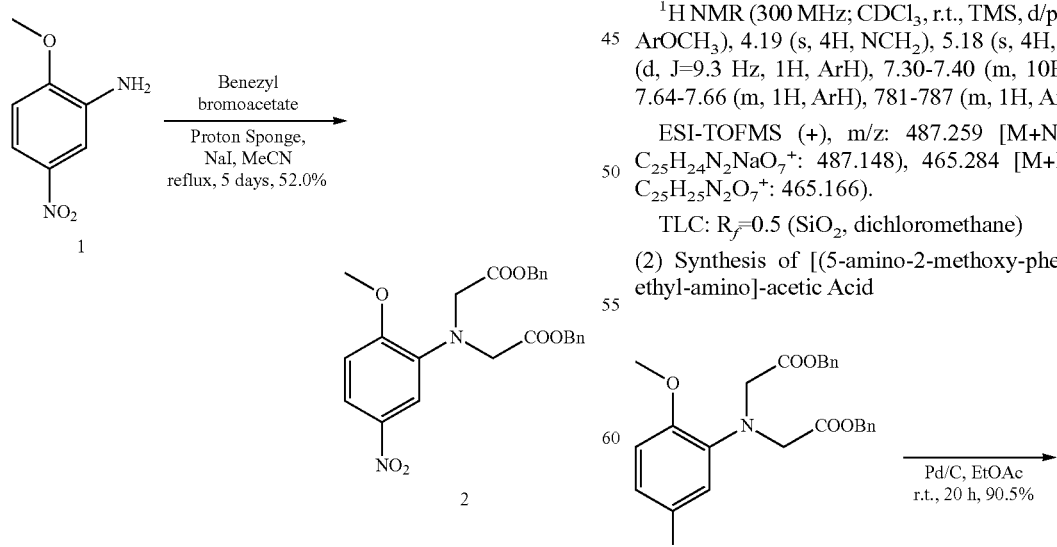

A mixture of 2-amino-4-nitroanisole (5.3 g, 31.5 mmol, 1.0 eq.), N,N,N',N'-tetramethyl-1,8-naphthalenediamine (proton sponge: 25.0 g, 116.7 mmol, 3.7 eq.), bromoacetic acid benzyl (20.2 g, 88.3 mmol, 2.8 eq.) and sodium iodide (5.7 g, 37.8 mmol, 1.2 eq.) in acetonitrile (430 mL) was heated to reflux under Ar atmosphere for 5 days. The solvent was evaporated under vacuum. The residue was dissolved in dichloromethane (1 L), and the mixture was sequentially washed with water (1 L), hydrochloric acid at pH 2 (1 L×2), water (1 L), aqueous NaHCO$_3$ solution (1 L) and with saturated aqueous NaCl solution (300 mL). The obtained organic solution was dried over Na$_2$SO$_4$. The solvent was evaporated under vacuum, and the residue was purified by column chromatography (SiO$_2$, hexane:dichloromethane=1:2-1:10-dichloromethane, v/v) to obtain yellow solids (yield: 52.0%).

$^1$H NMR (300 MHz; CDCl$_3$, r.t., TMS, d/ppm) 3.72 (s, 3H, ArOCH$_3$), 4.19 (s, 4H, NCH$_2$), 5.18 (s, 4H, OCH$_2$Ar), 6.81 (d, J=9.3 Hz, 1H, ArH), 7.30-7.40 (m, 10H, benzyl ArH), 7.64-7.66 (m, 1H, ArH), 781-787 (m, 1H, ArH).

ESI-TOFMS (+), m/z: 487.259 [M+Na]$^+$ (calcd. for C$_{25}$H$_{24}$N$_2$NaO$_7$$^+$: 487.148), 465.284 [M+H]$^+$ (calcd. for C$_{25}$H$_{25}$N$_2$O$_7$$^+$: 465.166).

TLC: R$_f$=0.5 (SiO$_2$, dichloromethane)

(2) Synthesis of [(5-amino-2-methoxy-phenyl)-carboxymethyl-amino]-acetic Acid

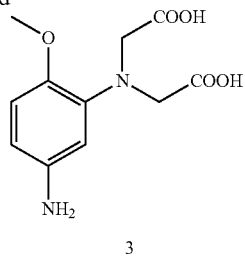

3

A solution of Compound 2 (3.0 g, 6.5 mmol, 1.0 eq.) in ethyl acetate (20 mL) was degassed under vacuum, and the atmosphere was replaced with Ar gas. The degassed solution was added to Pd/C (Pd content: 10 wt %, 2.0 g), and the Ar gas was replaced with hydrogen gas. The reaction mixture was stirred under hydrogen gas atmosphere for 20 hours at room temperature. The reaction mixture was filtered through a Celite plate, and the residue was washed with ethyl acetate (20 mL). A mixture of the resulting residue and methanol (100 mL) was filtered again through a Celite plate to remove the catalyst, and the filtrate was concentrated under vacuum to obtain a dark brown oily product (yield: 90.5%).

$^1$H NMR (300 MHz; D$_2$O, r.t., TMS, d/ppm) 3.79 (s, 3H, ArOCH$_3$), 4.06 (s, 4H, NCH$_2$), 7.64-7.67 (s, 1H, ArH), 6.90-6.95 (m, 1H, ArH), 7.05 (d, J=8.7 Hz, 1H, ArH).

ESI-TOFMS (+), m/z: 277.096 [M+Na]$^+$ (calcd. for C$_{11}$H$_{14}$N$_2$NaO$_5$$^+$: 277.079), 255.115 [M+H]$^+$ (calcd. for C$_{11}$H$_{15}$N$_2$O$_5$$^+$: 255.098).

TLC: R$_f$=0.7 (reverse phase, methanol:water=1:1, v/v)

(3) Synthesis of {bis-[2-({[3-(bis-carboxymethyl-amino)-4-methoxy-phenylcarbamoyl]-methyl}-carboxymethyl-amino)-ethyl]-amino}-acetic Acid

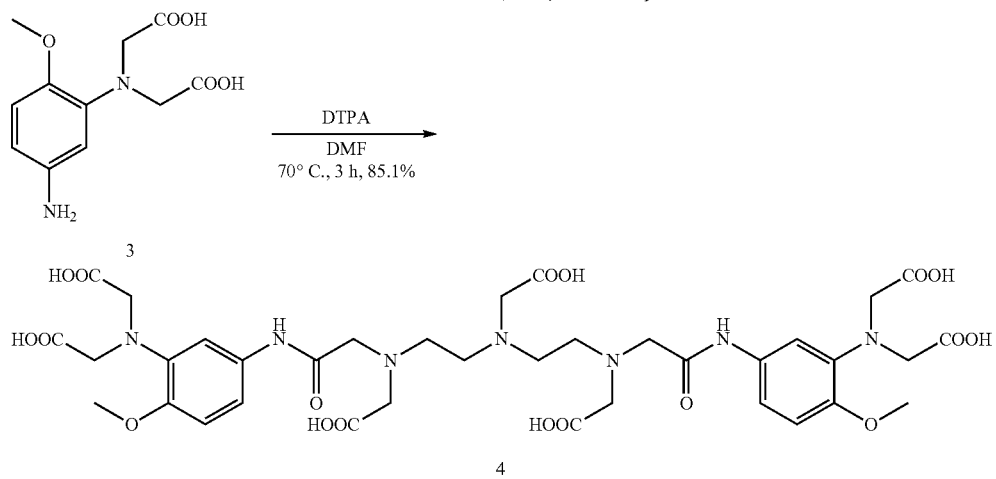

To a mixture of diethylenetriamine pentaacetic acid dianhydride (309.2 mg, 0.87 mmol, 1.0 eq.) and anhydrous N,N-dimethylformamide (3.0 mL), Compound 3 (440.0 mg, 1.7 mmol, 2.0 eq.) was added, and the resulting mixture was stirred under Ar atmosphere at 70° C. for 3 hours. The reaction mixture was evaporated under vacuum and the residue was purified by HPLC reverse phase column (methanol:water:trifluoroacetic acid=3:2:0.01, v/v, flow rate: 3.5 mL/min, retention time: 43 minutes) to obtain brown solids (yield: 85.1%).

$^1$H NMR (300 MHz; CD$_3$OD, r.t., TMS, d/ppm) 3.35-3.45 (m, 8H, NCH$_2$CH$_2$N), 3.73 (s, 4H, NCH$_2$CONH), 3.77 (s, 2H, center NCH$_2$COOH), 3.84 (s, 6H, OCH$_3$), 4.04 (s, 8H, ArNCH$_2$COOH), 4.05-4.15 (m, 4H, NCH$_2$COOH), 6.77 (d, J=8.5 Hz, 2H, ArH), 7.00-7.05 (m, 2H, ArH), 7.06 (s, 2H, ArH).

ESI-TOFMS (+), m/z: 452.738 [M+K+H]$^{2+}$ (calcd. for C$_{36}$H$_{48}$KN$_7$O$_{18}$$^{2+}$: 452.634), 463.731 [M+K+Na]$^{2+}$ (calcd. for C$_{36}$H$_{48}$KN$_7$NaO$_{18}$$^{2+}$: 463.625), 866.527 [M+H]$^+$ (calcd. for C$_{36}$H$_{48}$N$_7$O$_{18}$$^+$: 866.306).

(4) Synthesis of {bis-[2-({[3-(bis-carboxymethyl-amino)-4-methoxy-phenylcarbamoyl]-methyl}-carboxymethyl-amino)-ethyl]-amino}-acetic Acid Gadolinium Complex (KMR-Ca001)

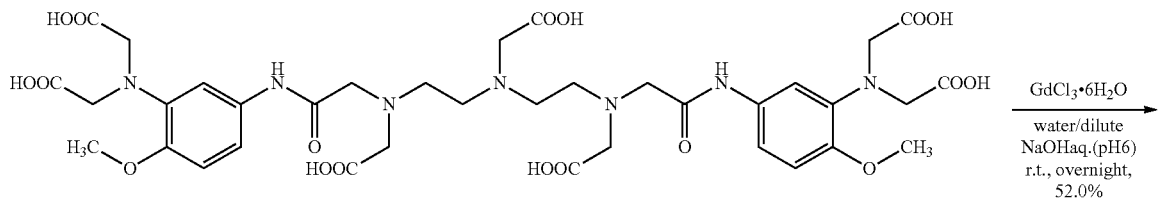

-continued

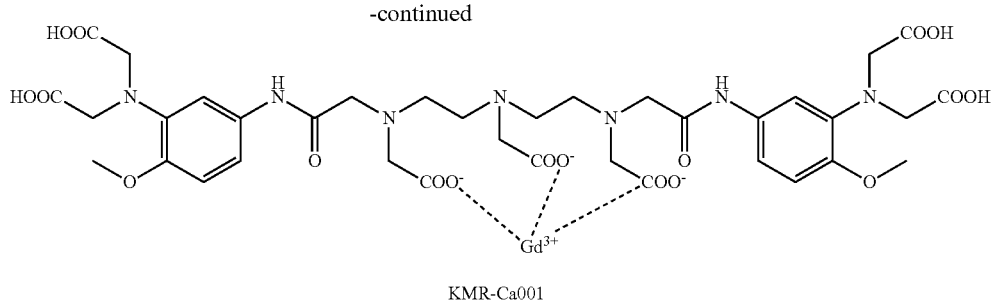

KMR-Ca001

To a solution of Compound 4 (21.0 mg, 24.0 μmol, 1.0 eq.) in water (1.0 mL), gadolinium(III) chloride hexahydrate (9.0 mg, 22.0 μmol, 0.9 eq.) was added, and the resulting mixture was stirred overnight at room temperature. During this reaction, aqueous dilute NaOH solution was added to keep the pH of the solution at 6. The reaction mixture was then evaporated under vacuum, and the residue was purified by HPLC reverse phase column (methanol:water=3:2, v/v, flow rate: 3.0 mL/min, retention time: 44 minutes) to obtain brown solids (yield: 52.0%).

ESI-TOFMS (+), m/z: 530.173 [M+K+H]$^{2+}$ (calcd. for $C_{36}H_{45}GdKN_7O_{18}^{2+}$: 530.084).

ESI-TOFMS (−): 508.747 [M−2H]$^{2−}$ (calcd. for $C_{36}H_{42}GdN_7O_{18}^{2+}$: 509.092), 338.827 [M−3H]$^{3−}$ (calcd. for $C_{36}H_{41}GdN_7O_{18}^{3−}$: 339.059).

Example 4

Performance of KMR-Ca001

KMR-Ca001 synthesized in Example 3 was examined for the relationship between the calcium ion concentration and longitudinal relaxation time by a conventional method. The measurement conditions were as follows:

[KMR-Ca001]: 0.3 mM
measured in 0.05 M Tris/HCl buffer at pH 7.2
$CaCl_2$ was used as $Ca^{2+}$.
measuring apparatus: NMS 120 minispec NMR ANALYZER produced by BRUKER (static magnetic field by permanent magnet was 40 MHz, apparatus for measuring longitudinal and transverse relaxation times) was used.
measuring temperature: 40° C.

Figure 5:
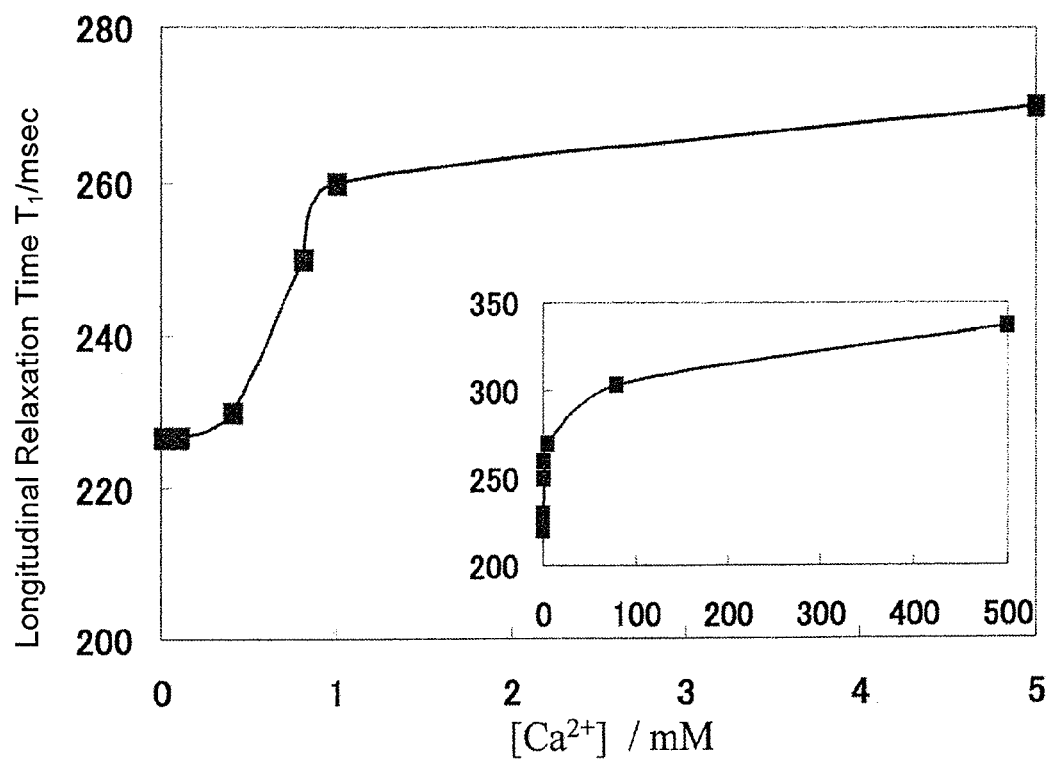
FIG. 5 shows the relationship between the concentration of calcium ion and longitudinal relaxation time of the calcium-responsive MRI probe according to the present invention prepared in an Example.

The results are shown in FIG. 5. As shown in FIG. 5, with KMR-Ca001, since the BAPTA and $Ca^{2+}$ formed a complex, access of water molecules to the gadolinium ion was inhibited and the longitudinal relaxation time was increased. The fact that the more the $Ca^{2+}$ ion exists, the easier the formation of the complex between BAPTA and $Ca^{2+}$ and so the shorter the longitudinal relaxation time can be seen from the figure. With KMR-Ca001, the longitudinal relaxation time increased maximally by 16 to 17%.

Example 5

Synthesis of Glucose-Responsive Gadolinium Complex Compound KMR-Glu001

According to the following scheme, a calcium ion-responsive gadolinium complex compound KMR-Glu001 was synthesized:

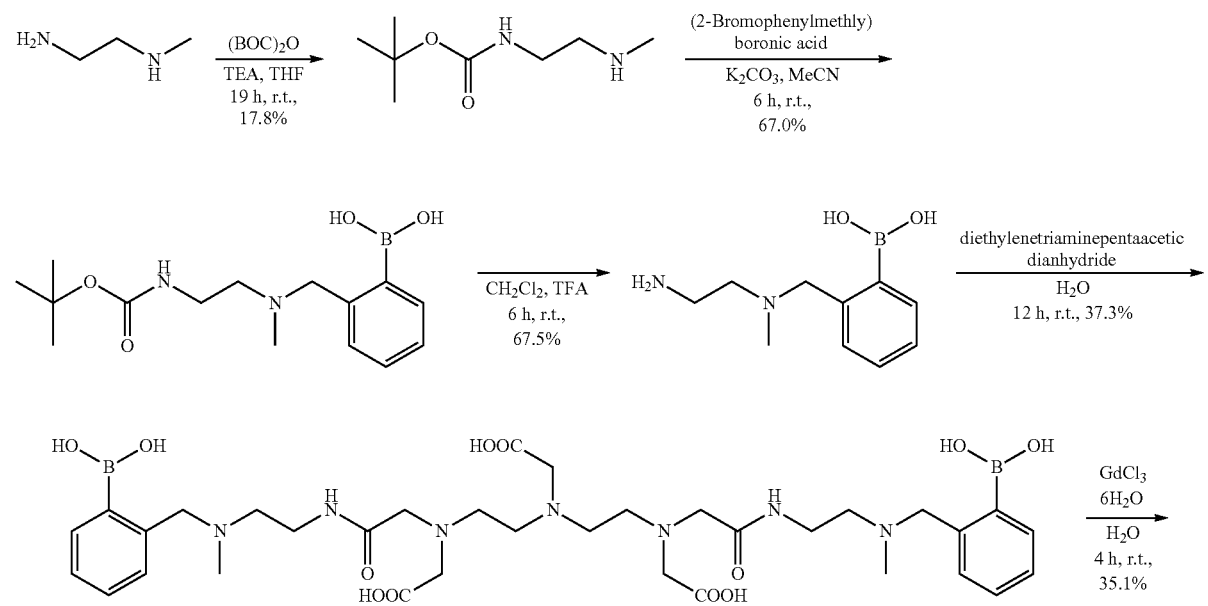

-continued

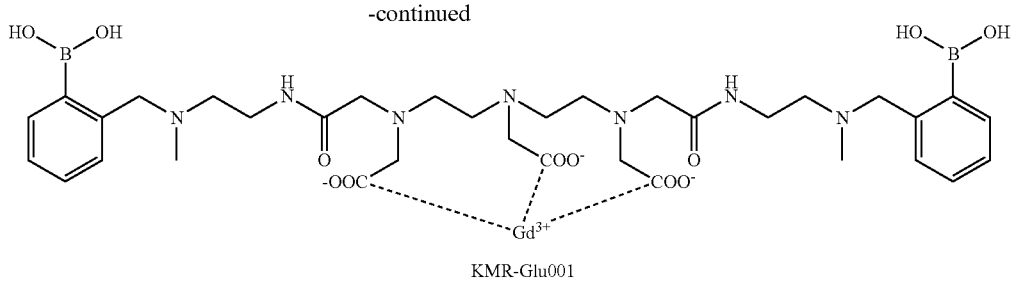

KMR-Glu001

Each step will now be described in detail.

(1) Synthesis of (2-methylamino-ethyl)-carbamic acid tert-butyl Ester (2)

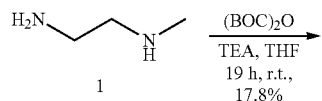

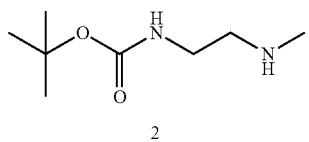

To a solution of N-methylethylenediamine 1 (10.0 g, 135 mmol, 1.0 eq.) in anhydrous THF (70 mL), triethylamine (37.6 ml, 270 mmol, 2.0 eq.) was added under Ar atmosphere at room temperature. A solution of di-t-butyl dicarbonate (32.5 g, 148 mmol, 1.1 eq.) in anhydrous THF (250 mL) was added dropwise at 0° C. from a dropping funnel for 30 minutes, and the resulting mixture was stirred at 0° C. for 30 minutes and then at room temperature for 19 hours. The reaction mixture was filtered and the solvent was evaporated under vacuum, followed by purification of the residue by column chromatography (SiO$_2$, chloroform:methanol: 30:1, v/v→chloroform:methanol:triethylamine=150:10:3, v/v) to obtain a yellow oily product (yield: 17.8%)

$^1$H-NMR (300 MHz; CDCl$_3$, r.t., TMS, d/ppm) 1.33 (s, 9H, —C(CH$_3$)$_3$), 2.76 (t, 2H, J=6.4 Hz, —CH$_2$CH$_2$NHCH$_3$), 2.86 (s, 3H, —NHCH$_3$), 3.21 (t, 2H, J=6.1 Hz, —CONHCH$_2$CH$_2$—).

ESI-TOFMS (+), m/z: 175.14[M+H]$^+$ (calcd. for C$_8$H$_{19}$N$_2$O$_2$$^+$ 175.14)

TLC; R$_f$=0.3 (br, chloroform/methanol=10:1, v/v)

(2) Synthesis of (2-{[(2-tert-butoxycarbonylamino-ethyl)-methyl-amino]-methyl}-phenyl)-boronic Acid (3)

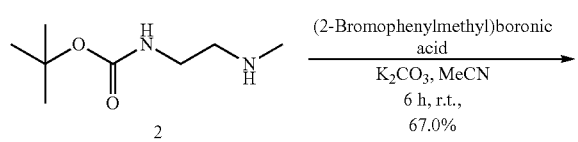

-continued

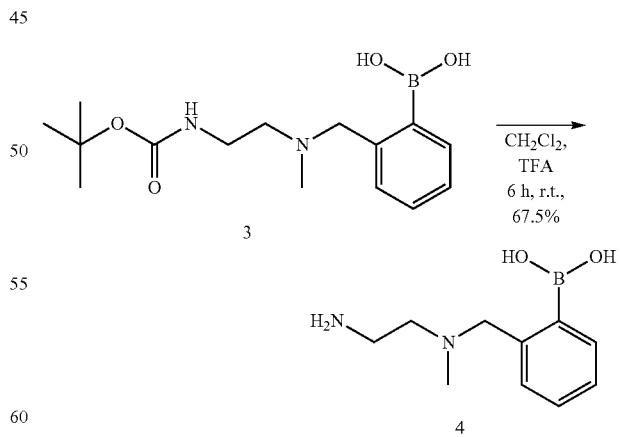

To a solution of Compound 2 (500 mg, 2.87 mmol, 1.0 eq.) in acetonitrile (15 mL), potassium carbonate (1.19 g, 8.61 mmol, 3.0 eq.) and (2-bromomethyl phenyl)boronic acid (0.617 g, 2.87 mmol, 1.0 eq.) were added, and the resulting mixture was stirred at room temperature for 4 hours. The solvent was evaporated under vacuum and the residue was washed with 0.5M hydrochloric acid and ethyl acetate. The pH of the aqueous solution was adjusted to 7.0 with NaOH. The solvent was washed with methyl chloride and brine. The organic solution was dried over Na$_2$SO$_4$. The solvent was evaporated under vacuum to obtain white solids (yield: 67.0%).

$^1$H-NMR (300 MHz; CD$_3$OD, r.t., TMS, d/ppm) 1.40 (s, 9H, —C(CH$_3$)$_3$), 2.88 (s, 3H, —CH$_2$NCH$_3$CH$_2$—), 3.14 (m, 2H, —CH$_2$N(CH$_3$)CH$_2$CH$_2$—), 3.64 (m, 2H, —CONHCH$_2$CH$_2$—), 3.95 (s, 2H, NCH$_2$Ar), 7.20-7.46 (m, 4H, ArH).

TLC; R$_f$=0.4 (br, chloroform:methanol=7:1, v/v)

(3) Synthesis of (2-{[(2-amino-ethyl)-methyl-amino]-methyl}-phenyl)-boronic Acid (4)

To a solution of Compound 3 (209 mg, 308 mmol, 1.0 eq.) in dichloromethane (2 mL), trifluoroacetic acid (2 mL) was added at 0° C., and the mixture was stirred at this temperature for 30 minutes and then at room temperature for 5 hours. The solvent was evaporated under vacuum and the residue was purified by preparative TLC (alumina, chloroform:methanol=5:1, v/v) to obtain yellow solids (yield: 67.5%).

$^1$H-NMR (300 MHz; CD$_3$OD, r.t., TMS, d/ppm) 2.45 (s, 3H, —CH$_2$NCH$_3$CH$_2$—), 2.92 (t, J=6.10 Hz, 2H, —CH$_2$NCH$_3$CH$_2$CH$_2$—), 3.01 (t, J=5.97 Hz, 2H, —CH$_2$CH$_2$NH$_2$), 4.02 (s, 2H, NCH$_2$Ar), 7.15-7.43 (m, 4H, ArH).

alumina TLC; R$_f$=0 (br, ethyl acetate)

(4) Synthesis of Compound 5

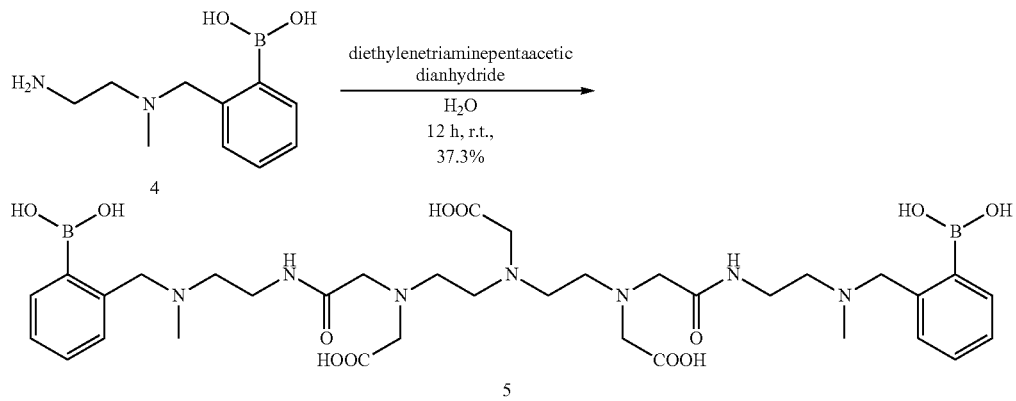

Compound 4 (800 mg, 3.85 mmol, 2.0 eq.) was dissolved in distilled water (60 mL), and the pH was adjusted to 8.5, followed by addition of diethylenetriamine pentaacetic acid dianhydride (638 mg, 1.92 mmol, 1.0 eq.) at 0° C. for 30 minutes. The reaction mixture was stirred at room temperature for 18 hours. The reaction mixture was evaporated under vacuum and the residue was purified by HPLC (methanol:water:trifluoroacetic acid=300:200:1) to obtain white solids (yield: 37.3%).

$^1$H-NMR (300 MHz; CD$_3$OD, r.t., TMS, d/ppm)
3.01 (s, 6H, —NCH$_3$CH$_2$Ar), 3.19 (m, 4H, —COCH$_2$N(CH$_2$COOH)CH$_2$CH$_2$—), 3.31 (m, 4H, —NCH$_3$CH$_2$CH$_2$—), 3.38 (m, 4H, —CH$_2$CH$_2$N(CH$_2$COOH)CH$_2$CH$_2$—), 3.77 (m, 4H, —NHCH$_2$CH$_2$—), 3.83 (s, 2H, NCH$_2$COOH), 3.92 (s, 4H, NCH$_2$CO—), 4.16 (s, 4H, NCH$_2$Ar), 4.37 (s, 4H, NCH$_2$COOH), 7.48-7.84 (m, 8H, ArH).

(5) Synthesis of KMR-Glu001

After adjusting the pH of a solution of Compound 5 (555 mg, 0.718 mmol, 1.0 eq.) in water (60 mL) to 6.0 to 7.0, gadolinium(III) chloride hexahydrate (289 mg, 0.789 mmol, 1.1 eq.) was added, and the resulting mixture was stirred at room temperature for 5 hours. The reaction mixture was evaporated under vacuum, and the residue was purified by HPLC (methanol:water=3:2) to obtain white solids (yield: 35.1%).

Identification of a gadolinium complex is difficult. This shows that the NMR spectrum is broadened due to the shortening of relaxation time by a paramagnetic material, and the peaks in ESI-TOFMS(+) spectrum are complicated. The present inventors confirmed both the broad NMR spectrum and the complicated peaks in MS spectrum to identify mass number of 497.21 and 1007.49. By this, the structure of KMR-Glu001 was identified.

Example 6

Synthesis of Glucose-Responsive Gadolinium Complex Compound KMR-Glu002

According to the following scheme, a calcium ion-responsive gadolinium complex compound KMR-Glu002 was synthesized:

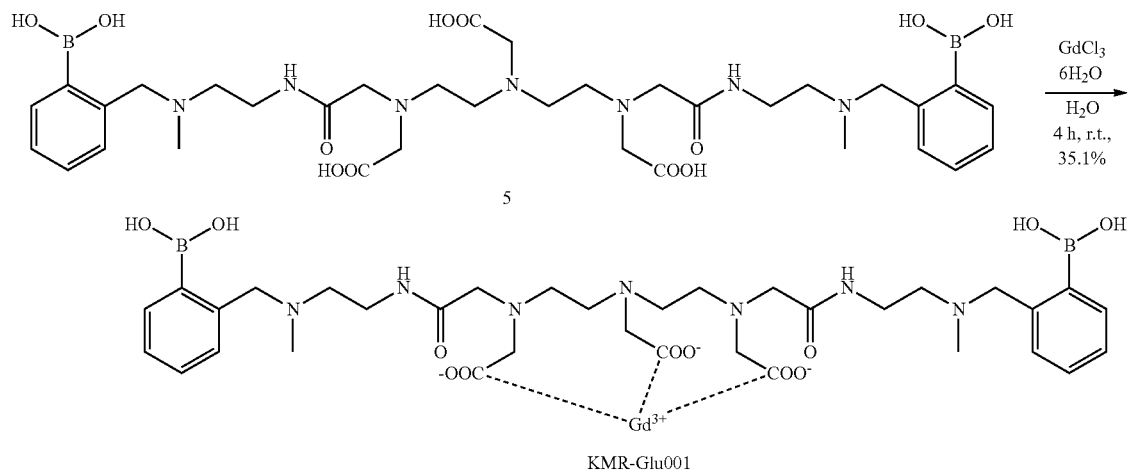

KMR-Glu001

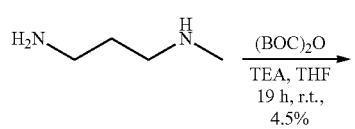
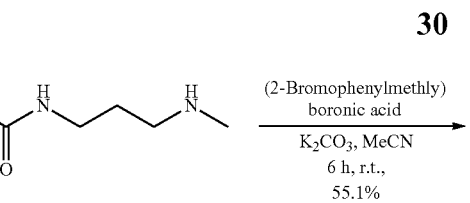
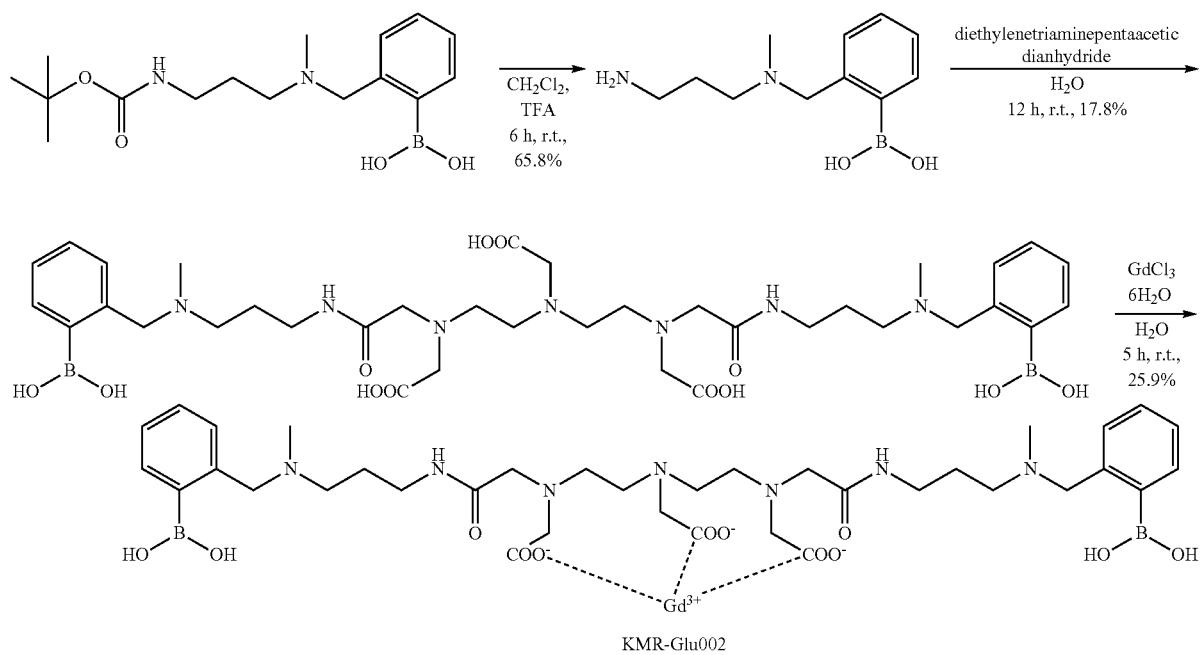

KMR-Glu002

Each step will now be described in detail.
(1) Synthesis of (3-methylamino-propyl)-carbamic acid tert-butyl Ester (8)

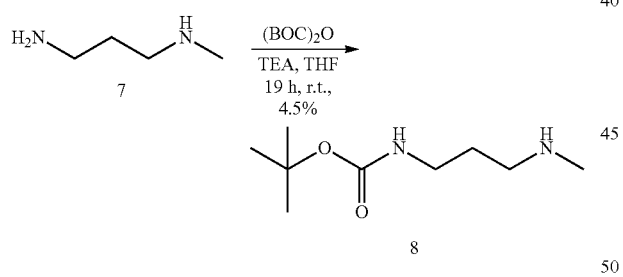

To a solution of N-methyl-1,3-propanediamine 7 (5.00 g, 56.7 mmol, 1.0 eq.) in anhydrous THF (40 mL), triethylamine (15.8 mL, 113 mmol, 2.0 eq.) was added under Ar atmosphere at room temperature. A solution of di-t-butyl dicarbonate (13.7 g, 62.4 mmol, 1.1 eq.) in anhydrous THF (100 mL) was added dropwise at 0° C. from a dropping funnel for 30 minutes, and the resulting mixture was stirred at 0° C. for 30 minutes and then at room temperature for 24 hours. The reaction mixture was filtered and the solvent was evaporated under vacuum, followed by purification of the residue by column chromatography (SiO$_2$, chloroform:methanol=30:1, v/v→chloroform:methanol:triethylamine=150:10:3, v/v) to obtain a yellow oily product (yield: 4.5%)

$^1$H-NMR (300 MHz; CDCl$_3$, r.t., TMS, d/ppm) 1.46 (s, 9H, —C(CH$_3$)$_3$), 1.70 (m, 2H, —CH$_2$CH$_2$CH$_2$—), 2.73 (t, 2H, J=6.90 Hz, —CH$_2$CH$_2$NHCH$_3$), 2.84 (s, 3H, —NHCH$_3$), 3.31 (m, 2H, —CONHCH$_2$CH$_2$—).

TLC; R$_f$=0.3 (br, chloroform:methanol=10:1, v/v)

(2) Synthesis of (2-{[(3-tert-butoxycarbonylamino-propyl)-methyl-amino]-methyl}-phenyl)-boronic Acid (9)

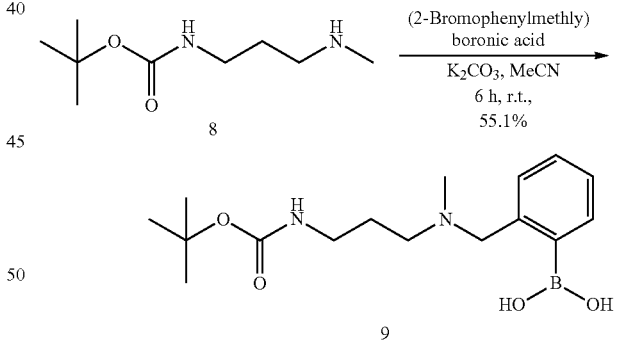

To a solution of Compound 8 (452 mg, 2.40 mmol, 1.0 eq.) in acetonitrile (15 mL), potassium carbonate (0.995 g, 7.20 mmol, 3.0 eq.) and (2-bromomethyl phenyl)boronic acid (567 mg, 2.64 mmol, 1.1 eq.) were added, and the resulting mixture was stirred at room temperature for 23 hours. The solvent was evaporated under vacuum and the residue was washed with 0.5M hydrochloric acid and ethyl acetate. The pH of the aqueous solution was adjusted to 7.0 with NaOH. The solvent was washed with methyl chloride and brine. The organic solution was dried over Na$_2$SO$_4$. The solvent was evaporated under vacuum to obtain white solids (yield: 55.1%).

TLC; R$_f$=0.2 (br, chloroform:methanol=7:1, v/v)

(3) Synthesis of (2-{[(3-amino-propyl)-methyl-amino]-methyl}-phenyl)-boronic Acid (10)

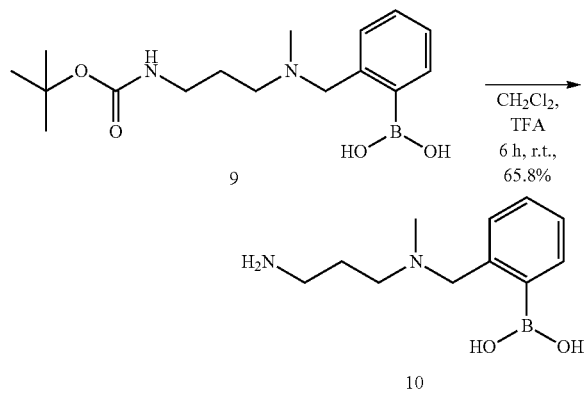

To a solution of Compound 9 (426 mg, 1.32 mmol, 1.0 eq.) in dichloromethane (4.5 mL), trifluoroacetic acid (4.5 mL) was added at 0° C., and the resulting mixture was stirred at this temperature for 30 minutes and then at room temperature for 6 hours. The solvent was evaporated under vacuum and the residue was purified by preparative TLC (alumina, chloroform:methanol=3:1, v/v) to obtain a brown oily product (yield: 65.8%).

$^1$H-NMR (300 MHz; $CD_3OD$, r.t., TMS, d/ppm) 2.02 (dd, J=7.4 Hz, 2H, —$CH_2CH_2CH_2$—), 2.60 (s, 3H, —$CH_2NCH_3CH_2$—), 2.93 (t, J=7.2 Hz, 2H, —$CH_2NCH_3CH_2CH_2$—), 2.95 (t, J=6.3 Hz, 2H, —$CH_2CH_2NH_2$), 4.01 (s, 2H, $NCH_2Ar$), 7.20-7.44 (m, 4H, ArH)

Alumina TLC; $R_f$=0.4 (br, chloroform:methanol=3:1, v/v)

Synthesis of Compound 11

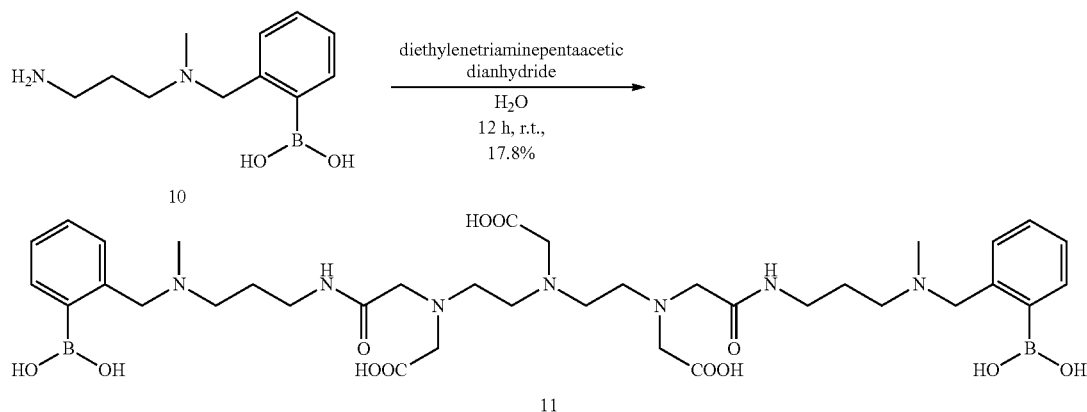

Compound 10 (446 mg, 2.01 mmol, 1.0 eq.) was dissolved in distilled water (20 mL), and the pH was adjusted to 8.5, followed by addition of diethylenetriamine pentaacetic acid dianhydride (790 mg, 2.21 mmol, 1.1 eq.) at 0° C. for 30 minutes. The reaction mixture was stirred at room temperature for 18 hours. The reaction mixture was evaporated under vacuum and the residue was purified by HPLC (methanol:water:trifluoroacetic acid=300:200:1) to obtain white solids (yield: 17.8%).

$^1$H-NMR (300 MHz; $CD_3OD$, r.t., TMS, d/ppm) 1.99 (dt, J=6.3 Hz, 4H, —$CH_2CH_2CH_2$—), 2.99 (s, 6H, —$CH_2NCH_3CH_2$—), 3.06 (t, J=6.84 Hz, 4H, —$CH_2NCH_3CH_2CH_2$—), 3.24 (m, 4H, —$COCH_2N(CH_2COOH)CH_2CH_2$—), 3.31 (m, 4H, —$CH_2CH_2N(CH_2COOH)CH_2CH_2$—), 3.50 (t, J=5.61 Hz, 4H, —$CH_2CH_2NH$—), 3.81 (s, 4H, $NCH_2CO$—), 3.86 (s, 2H, $NCH_2COOH$), 4.10 (s, 4H, $NCH_2Ar$), 4.32 (s, 4H, $NCH_2COOH$), 7.44-7.89 (m, 8H, ArH).

(5) Synthesis of KMR-Glu002

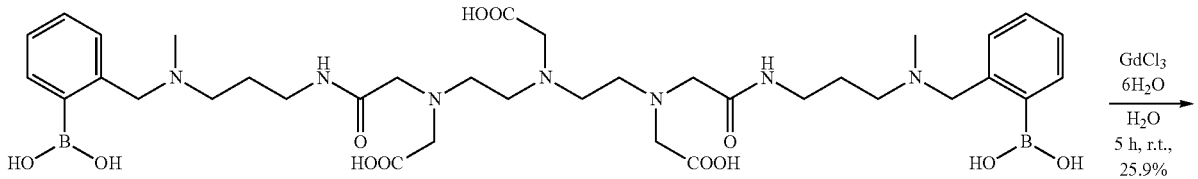

-continued

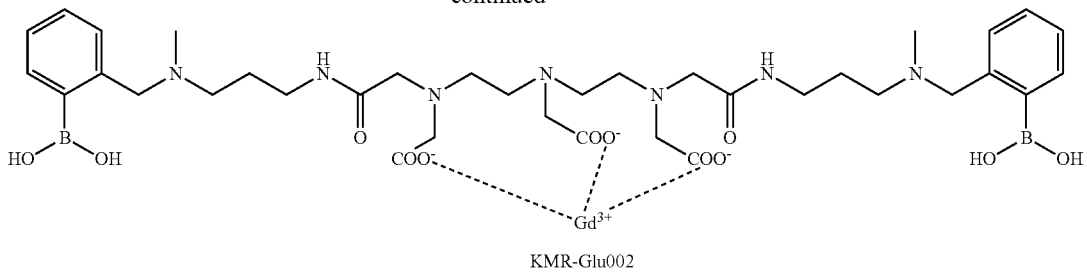

KMR-Glu002

After adjusting the pH of a solution of Compound 11 (286 mg, 0.357 mmol, 1.0 eq.) in water (22 mL) to 6.0 to 7.0, gadolinium(III) chloride hexahydrate (148 mg, 0.397 mmol, 1.1 eq.) was added, and the resulting mixture was stirred at room temperature for 5 hours. The reaction mixture was evaporated under vacuum, and the residue was purified by HPLC (methanol:water=3:2) to obtain white solids (yield: 25.9%).

As described above for KMR-Glu001, the present inventors confirmed both the broad NMR spectrum and the complicated peaks in MS spectrum to identify mass number of 528.69 and 1035.45. By this, the structure of KMR-Glu002 was identified.

Example 7

Performance of KMR-Glu001 and KMR-Glu002

KMR-Glu001 and KMR-Glu002 synthesized in Examples 5 and 6 were examined for the relationship between the glucose concentration and longitudinal relaxation time by a conventional method. The measurement conditions were as follows:

[KMR-Glu001], [KMR-Glu002]: 1.0 mM
measured in 0.1M phosphate buffer at pH 8.0
measuring apparatus: NMS 120 minispec NMR ANALYZER produced by BRUKER (static magnetic field by permanent magnet was 40 MHz, apparatus for measuring longitudinal and transverse relaxation times) was used.
measuring temperature: 40° C.

Figure 6:
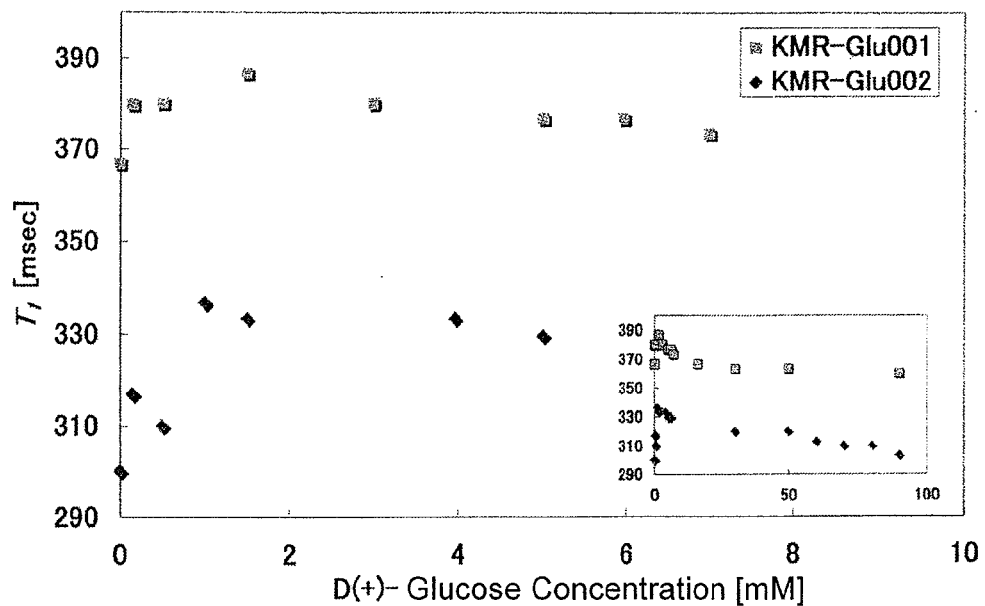
FIG. 6 shows the relationship between the concentration of glucose and longitudinal relaxation time of the glucose-responsive MRI probe according to the present invention prepared in an Example.

The results are shown in FIG. 6. When the glucose was not more than about 1 equivalent with respect to the MRI probe, two boronic acid molecules recognized four sites of one glucose molecule, so that access of water molecules to the gadolinium ion was inhibited and the longitudinal relaxation time monotonically increased. In the presence of an excess glucose with respect to the MRI probe, it is thought that two boronic acid molecules recognized 4 sites of one glucose molecule, and further a state wherein one boronic acid molecule recognized two sites of one glucose molecule. When this 1:1 complex is formed, water molecules can access to the gadolinium ion, so that the longitudinal relaxation time is decreased accordingly. The fact that the more the existing glucose, the shorter the longitudinal relaxation time can also be seen from the figure. Comparing KMR-Glu001 and KMR-Glu002, although the spacer between the gadolinium complex and the boronic acid is longer in KMR-Glu002 than in KMR-Glu001. The longitudinal relaxation time was increased maximally by 5% with KMR-Glu001 and maximally by 11% with KMR-Glu002. Considering these results, it can be seen that with the KMR-Glu molecules which recognize glucose, the length of the spacer greatly influences on the change in the longitudinal relaxation time when responding to glucose, so that contrast is easily generated in imaging.

Example 8

Solutions of KMR-K001 (1.0 mM) and KCl (0, 0.01, 0.1, 0.3, 0.6, 0.9, 1.2, 1.5, 1.8, 2.4, 3.0, 10, 30. 100 mM) in 0.05M Tris/HCl buffer, pH 7.4, were prepared in an amount of 2 mL, respectively. Each solution was measured for the longitudinal relaxation time T1 three times using NMS 120 Minispec NMR ANALYZER (0.47 T, 40° C., IR pulse). Then each solution was sequentially diluted to attain KMR-K001 concentrations of 0.9 mM and 0.8 mM, respectively, and the longitudinal relaxation time T1 was measured therefor. By taking [KMR-K001] along the abscissa and taking 1/T1 along the ordinate, relaxivity $R_1$ was determined from the slope. Measurements of the longitudinal relaxation time were carried out in the same manner using $CaCl_2$, $MgCl_2$ or $FeCl_3$.

Figure 7:
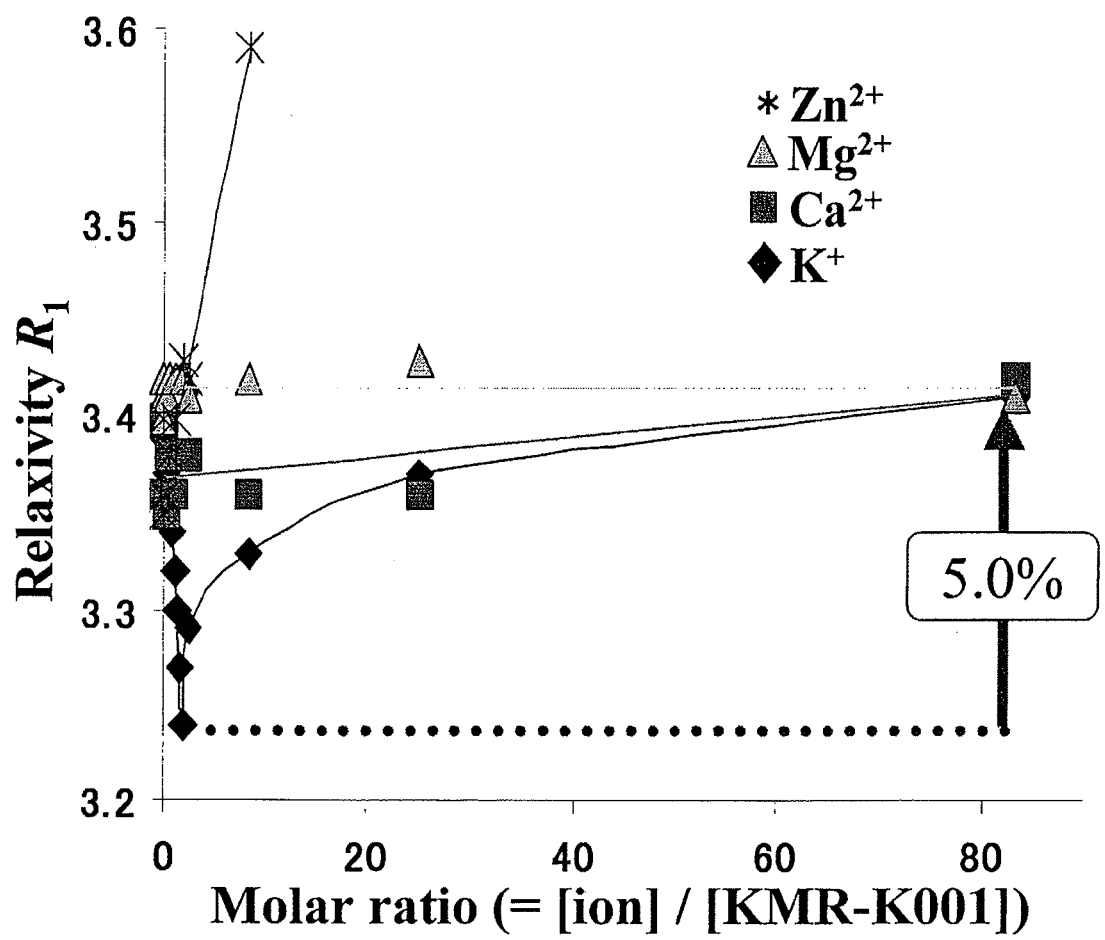
FIG. 7 shows the changes in relaxivity of the potassium-responsive MRI probe prepared in an Example depending on the abundance of respective ions.

The results are shown in FIG. 7. It can be seen from FIG. 7 that KMR-K001 is an MRI contrast agent which selectively responds to potassium ion. In the presence of zinc ion, since ligand exchange occurs between the gadolinium ion and zinc ion and gadolinium ion is liberated, the relaxivity is sharply increased.

Example 9

Solutions of KMR-Ca001 (0.6 mM) and $CaCl_2$ (0, 0.01, 0.1, 0.2, 0.3, 0.4, 0.5, 0.6, 0.7, 0.8, 1.0, 1.2, 3.0, 10, 30, 100 mM) in 0.05M Tris/HCl buffer, pH 7.4, were prepared in an amount of 2 mL, respectively. Each solution was measured for the longitudinal relaxation time T1 three times using NMS 120 Minispec NMR ANALYZER (0.47 T, 40° C., IR pulse). Then each solution was sequentially diluted to attain KMR-K001 concentrations of 0.45 mM and 0.35 mM, respectively, and the longitudinal relaxation time T1 was measured therefor in the same manner. By taking [KMR-Ca001] along the abscissa and taking 1/T1 along the ordinate, relaxivity $R_1$ was determined from the slope. Measurements of the longitudinal relaxation time were carried out in the same manner using NaCl, $MgCl_2$ or $FeCl_3$.

Figure 8:
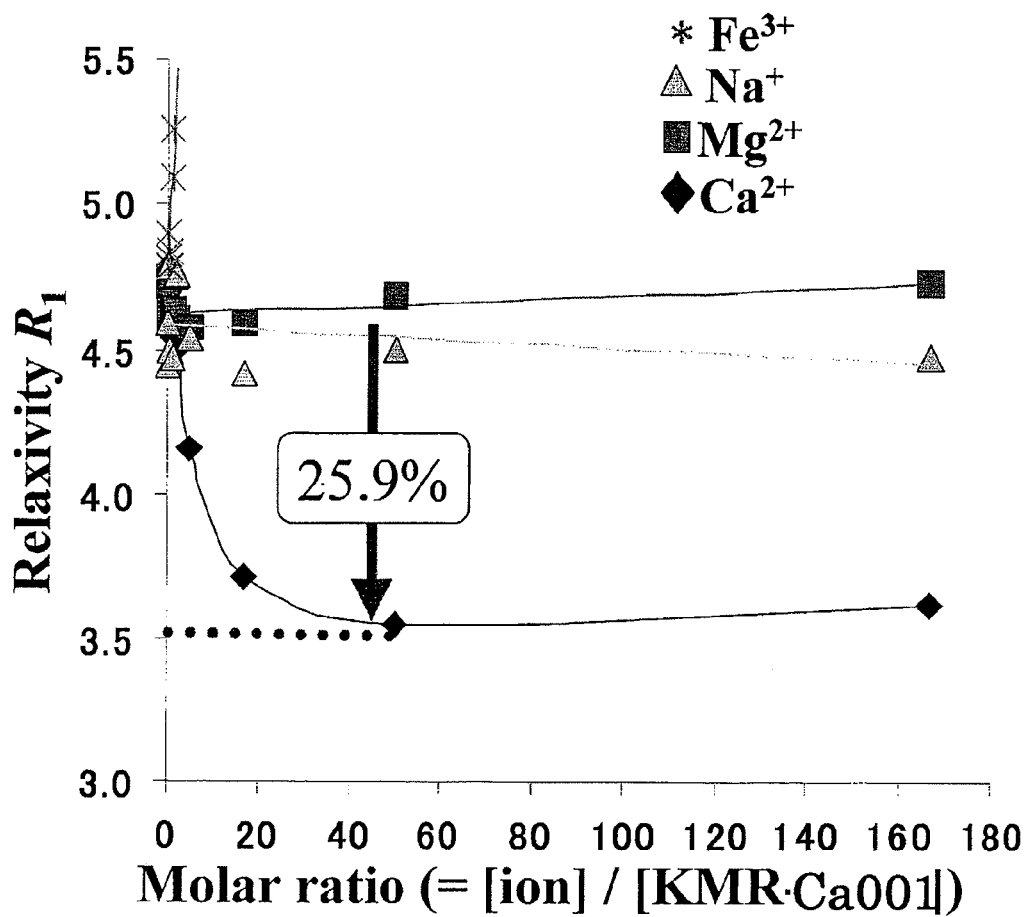
FIG. 8 shows the changes in relaxivity of the calcium-responsive MRI probe prepared in an Example depending on the abundance of respective ions.

The results are shown in FIG. 8. It can be seen from FIG. 8 that KMR-Ca001 is an MRI contrast agent which selectively responds to calcium ion. In the presence of iron ion, since the iron ion per se has a relaxing capability, the relaxivity is sharply increased.

Example 10

Water, solutions containing KMR-Ca001 alone at concentrations of 0.1, 0.3, 0.6, 1.0 and 3.0 mM, respectively, and solutions containing 0.3 mM KMR-Ca001 and $CaCl_2$ at concentrations of 0.5, 0.6, 0.8, 1.0, 10.0, 20.0, 50.0, 80.0 mM, respectively, in 0.05M Tris/HCl buffer, pH 7.4, were prepared, and placed in glass tubes, respectively. These glass tubes were stood on agar contained in a Tupperware, and $T_1$-weighted images were obtained by $T_1$-weighted GRE using a 1.5T MR scanner (Signa Horzon LX, produced by GE Yokogawa Medical Systems).

As a result, as KMR-Ca001 increased, the $T_1$-weighted images became whiter, so that it was confirmed that KMR-Ca001 functioned and effective as an MRI contrast agent. The $T_1$-weighted images of the solutions containing 0.3 mM KMR-Ca001 to which calcium ion was added, as the calcium ion increases, coordination of water to gadolinium ion was more inhibited, so that $T_1$-weighted image became darker. By this, it was confirmed that KMR-Ca001 is an MRI contrast agent which responds to calcium ion concentration.

Example 11

Solutions of KMR-Glu001 (1.0 mM) and D-glucose (0, 0.15, 0.5, 1.0, 1.5, 2.0, 3.0, 4.0, 5.0, 6.0, 0.7, 8.0, 9.0, 10, 16, 30, 50, 77, 80, 90, 100 mM) in 0.05M phosphate buffer, pH 8.0, were prepared in an amount of 2 mL, respectively. Each solution was measured for the longitudinal relaxation time T1 three times using NMS 120 Minispec NMR ANALYZER (0.47 T, 40° C., IR pulse). $R_1$ was determined from $1/T_1$.

Figure 9:
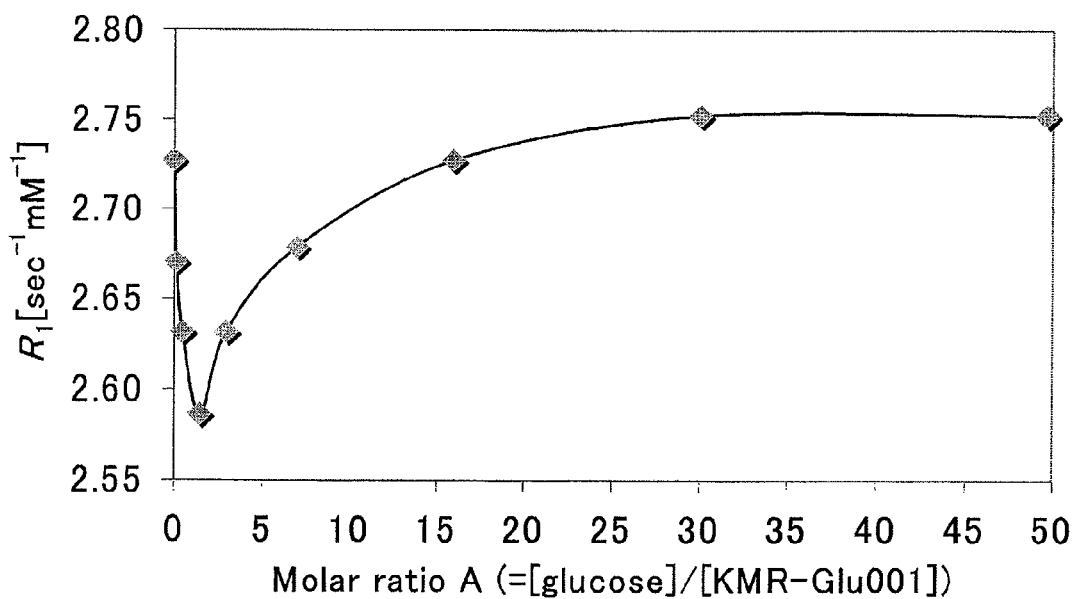
FIG. 9 shows the changes in relaxivity of the glucose-responsive MRI probe prepared in an Example depending on the abundance of glucose.

The results are shown in FIG. 9. It can be seen from FIG. 9 that KMR-Glu001 is an MRI contrast agent which responds to glucose. It can be seen that when glucose existed in excess with respect to KMR-Glu001, the relaxivity was increased, so that KMR-Glu001 exhibits positive response to glucose concentration.

Example 12

Water, solutions containing KMR-Glu001 alone at concentrations of 0.1, 0.3, 0.6, 1.0 and 3.0 mM, respectively, and solutions containing 0.3 mM KMR-Glu001 and glucose at concentrations of 0.1, 0.3, 1.0, 3.0, 10.0 mM, respectively, in 0.05M phosphate buffer, pH 8.0, were prepared, and placed in glass tubes, respectively. These glass tubes were stood on agar contained in a Tupperware, and $T_1$-weighted images were obtained by $T_1$-weighted GRE using a 1.5T MR scanner (Signa Horzon LX, produced by GE Yokogawa Medical Systems).

Figure 10:
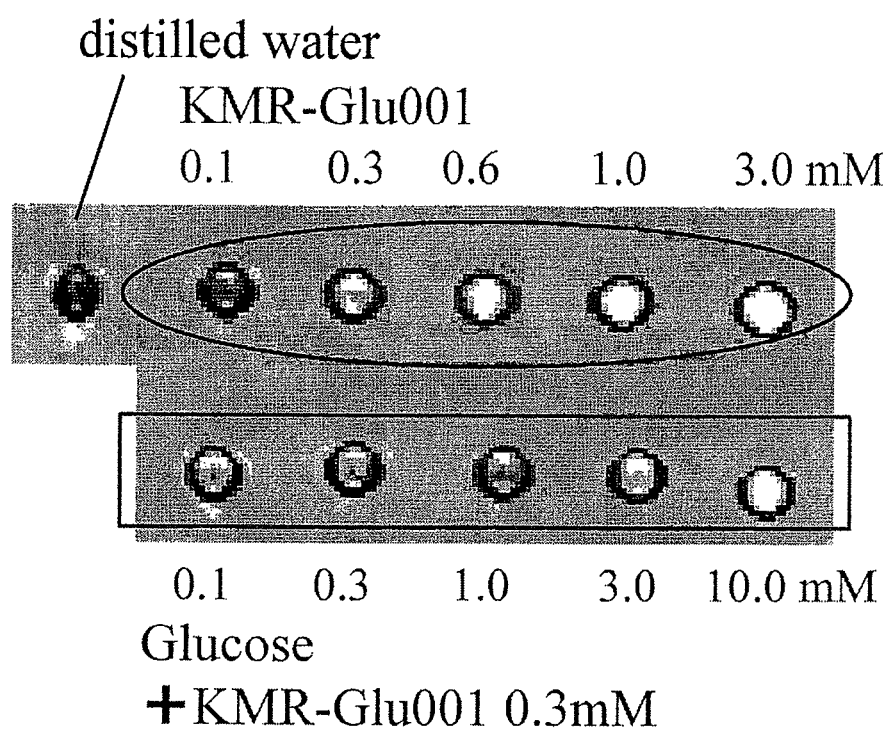
FIG. 10 shows T1-weighted images of the glucose-responsive MRI probe prepared in an Example.

The results are shown in FIG. 10. The upper row in FIG. 10 shows the results wherein the KMR-Glu001 concentration was changed from 0.1 to 3.0 mM. As KMR-Glu001 increases, the $T_1$-weighted images became whiter, so that it was confirmed that KMR-Glu001 functioned and effective as an MRI contrast agent. The lower row in FIG. 10 shows T1-weighted images when glucose was added to 0.3 mM KMR-Glu001. With increase in the glucose, up to the point of KMR-Glu001: glucose=1:1, coordination of water to the gadolinium ion was inhibited, so that the $T_1$-weighted images became darker. On the other hand, when glucose existed in excess with respect to KMR-Glu001, coordination of water to the gadolinium ion was again attained, so that the $T_1$-weighted images became whiter. By this, it was confirmed that KMR-Glu001 is an MRI contrast agent which responds to glucose concentration and that when glucose existed in excess with respect to KMR-Glu001, KMR-Glu001 exhibits positive response to glucose concentration.

The invention claimed is:

1. A method for measuring glucose in a living body, said method comprising administering to a living body a glucose-responsive MRI probe comprising a gadolinium complex compound represented by the following Formula (1) or (2):

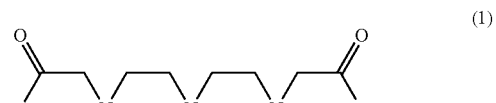

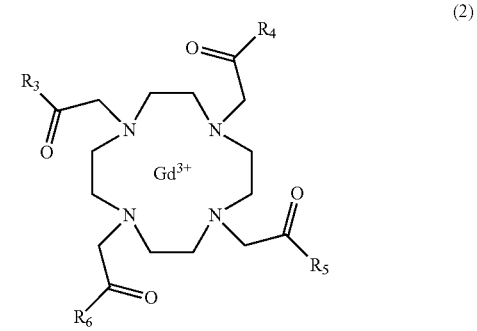

wherein in Formulae (1) and (2), $R_1$ and $R_2$ are independently a group represented by the following Formulae (6) or (7); two of $R_3$, $R_4$, $R_5$ and $R_6$ are —OH and the other two of them are independently a group represented by said Formulae (6) or (7):

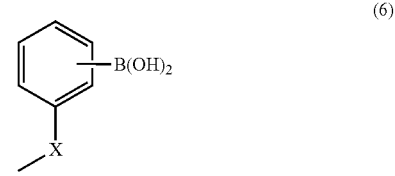

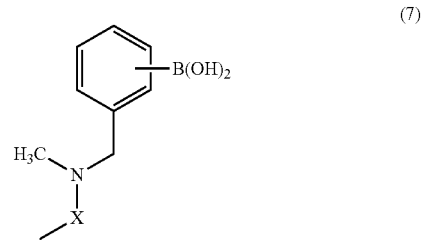

wherein in Formulae (6) and (7), X is an alkylene group (wherein one or more carbon atoms constituting the alkylene chain may be an oxygen atom(s), nitrogen atom(s), sulfur atom(s), silicon atom(s), phosphorus atom(s) or carbonyl group(s)) imaging the living body with MRI apparatus; determining a longitudinal relaxation time for the glucose-responsive MRI probe complexed with glucose, thereby providing an index for measuring glucose in the living body.

2. The method according to claim 1, wherein in said Formula (6) or (7), X is a $C_1$-$C_{10}$ alkylene group (wherein one or more carbon atoms constituting the alkylene chain may be an oxygen atom(s), nitrogen atom(s), sulfur atom(s), silicon atom(s), phosphorus atom(s) or carbonyl group(s)).

3. The method according to claim 2, wherein in said Formulae (1) and (2), $R_1$ and $R_2$ are independently a group represented by said Formula (7); two of $R_3$, $R_4$, $R_5$ and $R_6$ are —OH and the other two of them are independently a group represented by said Formula (7).

4. The method according to claim 3, wherein said group represented by said Formula (7) is a group represented by the following Formula (11):

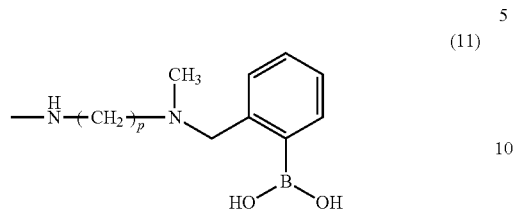

(11)

(wherein in Formula (11), p is an integer of 2 or 3).

5. The method according to claim 1, wherein said gadolinium complex is represented by said Formula (1).

6. The method according to claim 2, wherein said gadolinium complex is represented by said Formula (1).

7. The method according to claim 3, wherein said gadolinium complex is represented by said Formula (1).

8. The method according to claim 4, wherein said gadolinium complex is represented by said Formula (1).

* * * * *